(12) United States Patent
Yamauchi et al.

(10) Patent No.: US 10,209,056 B2
(45) Date of Patent: Feb. 19, 2019

(54) INTERFERENCE OBSERVATION DEVICE

(71) Applicant: HAMAMATSU PHOTONICS K.K., Hamamatsu-shi, Shizuoka (JP)

(72) Inventors: Toyohiko Yamauchi, Hamamatsu (JP); Hidenao Yamada, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/545,356

(22) PCT Filed: Dec. 14, 2015

(86) PCT No.: PCT/JP2015/084917
§ 371 (c)(1),
(2) Date: Jul. 21, 2017

(87) PCT Pub. No.: WO2016/121248
PCT Pub. Date: Aug. 4, 2016

(65) Prior Publication Data
US 2017/0356735 A1    Dec. 14, 2017

(30) Foreign Application Priority Data
Jan. 30, 2015   (JP) .............................. 2015-016266

(51) Int. Cl.
*G01B 9/02*    (2006.01)
*G01N 21/45*   (2006.01)
(Continued)

(52) U.S. Cl.
CPC ....... *G01B 9/0203* (2013.01); *G01B 9/02015* (2013.01); *G01B 9/02049* (2013.01);
(Continued)

(58) Field of Classification Search
CPC ............ G01B 9/02015; G01B 9/02049; G01N 21/45; G01N 21/00
See application file for complete search history.

(56) References Cited

U.S. PATENT DOCUMENTS 5,847,827 A * 12/1998 Fercher ................. A61B 3/102
356/493
7,812,959 B1 * 10/2010 Kim ...................... G01B 9/021
356/458

(Continued)

FOREIGN PATENT DOCUMENTS

| CN | 101033937 A | 9/2007 |
| JP | H05-79815 A | 3/1993 |

(Continued)

OTHER PUBLICATIONS

International Preliminary Report on Patentability dated Aug. 10, 2017 for PCT/JP2015/084917.

(Continued)

*Primary Examiner* — Jonathan Hansen
(74) *Attorney, Agent, or Firm* — Drinker Biddle & Reath LLP

(57) ABSTRACT

An interference observation apparatus includes a light source, a splitting beam splitter, a combining beam splitter, a beam splitter, a mirror, a beam splitter, a mirror, a piezo element, a stage, an imaging unit, an image acquisition unit, and a control unit. An interference optical system from the splitting beam splitter to the combining beam splitter forms a Mach-Zehnder interferometer. The mirror freely moves in a direction perpendicular to a reflecting surface of the mirror. The total number of times of respective reflections of first split light and second split light in the interference optical system is an even number.

7 Claims, 12 Drawing Sheets

(51) Int. Cl.
G02B 21/00 (2006.01)
G01N 33/483 (2006.01)
G02B 21/06 (2006.01)
G02B 21/36 (2006.01)

(52) U.S. Cl.
CPC ......... *G01N 21/45* (2013.01); *G01N 33/4833* (2013.01); *G02B 21/00* (2013.01); *G02B 21/06* (2013.01); *G02B 21/361* (2013.01); *G01B 9/02042* (2013.01)

(56) References Cited

U.S. PATENT DOCUMENTS

| | | |
|---|---|---|
| 8,248,593 B2 | 8/2012 | Yamauchi et al. |
| 2002/0196450 A1 | 12/2002 | Olszak et al. |
| 2005/0105097 A1 | 5/2005 | Fang-Yen et al. |
| 2009/0073450 A1 | 3/2009 | Boyd et al. |
| 2010/0309479 A1 | 12/2010 | Yamauchi et al. |

FOREIGN PATENT DOCUMENTS

| | | |
|---|---|---|
| JP | H10-232204 A | 9/1998 |
| JP | 2001-4538 A | 1/2001 |
| JP | 2005-345288 A | 12/2005 |
| JP | 4132308 B2 | 8/2008 |
| JP | 2009-116082 A | 5/2009 |
| JP | 2010-139326 A | 6/2010 |
| JP | 2012-132838 A | 7/2012 |
| JP | 2015-503128 A | 1/2015 |
| WO | WO-2013/095282 A2 | 6/2013 |

OTHER PUBLICATIONS

International Preliminary Report on Patentability dated Aug. 10, 2017 for PCT/JP2015/084919.

Pinhas Girshovitz et al., "Generalized cell morphological parameters based on interferometric phase microscopy and their application to cell life cycle characterization," Biomedical Optics Express, 2012, pp. 1757-1773, vol. 3, No. 8.

A. A. Freschi et al., "Adjustable phase control in stabilized interferometry," Optics Letters, 1995, pp. 635-637, vol. 20, No. 6.

Toyohiko Yamauchi et al., "Low-coherent quantitative phase microscope for nanometer-scale measurement of living cells morphology," Optics Express, 2008, pp. 12227-12238, vol. 16, No. 16.

Hidenao Iwai et al., "Quantitative phase imaging using actively stabilized phase-shifting low-coherence interferometry," Optics Letters, 2004, pp. 2399-2401, vol. 29, No. 20.

Ichirou Yamaguchi et al., "Active phase-shifting interferometers for shape and deformation measurements," Optical Engineering, 1996, pp. 2930-2937, vol. 35, No. 10.

Gordon S. Kino et al., "Mirau correlation microscope," Applied Optics, 1990, pp. 3775-3783, vol. 29, No. 26.

Michael B. Sinclair et al., "Long-working-distance incoherent-light interference microscope," Applied Optics, 2005, pp. 7714-7721, vol. 44, No. 36.

Tong Zhang et al., "Three-dimensional microscopy with phase-shifting digital holography," Optics Letters, 1998, pp. 1221-1223, vol. 23, No. 15.

Christopher Fang-Yen et al., "Imaging voltage-dependent cell motions with heterodyne Mach-Zehnder phase microscopy," Optics Letters, 2007, pp. 1572-1574, vol. 32, No. 11.

Christopher J. Mann et al., "High-resolution quantitative phase-contrast microscopy by digital holography," Optics Express, 2005, pp. 8693-8698, vol. 13, No. 22.

Lluís Martínez-León et al., "Applications of short-coherence digital holography in microscopy," Applied Optics, 2005, pp. 3977-3984, vol. 44, No. 19.

Office Action dated Oct. 30, 2018 that issued in U.S. Appl. No. 15/546,168.

* cited by examiner (a)

(b)

(a)

(b)

(a)

(b)

INTERFERENCE OBSERVATION DEVICE

TECHNICAL FIELD

The present invention relates to an interference observation apparatus.

BACKGROUND ART

An interference observation apparatus for acquiring an interference image of an observation object causes light reflected by or transmitted through the observation object and reference light to interfere with each other using an optical system of a Michelson interferometer or a Mach-Zehnder interferometer, so that the interference image of the observation object can be acquired. The interference observation apparatus disclosed in Non Patent Document 1 uses an optical system of the Mach-Zehnder interferometer, and splits light output from a light source into first split light and second split light, transmits the first split light on the observation object, and combines the first split light and the second split light to acquire an image of interference light generated by the combining.

CITATION LIST

Non Patent Literature

Non Patent Document 1: Pinhas Girshovitz, et al, "Generalized cell morphological parameters based on interferometric phase microscopy and their application to cell life cycle characterization," BIOMEDICAL OPTICS EXPRESS, Vol. 3, No. 8, pp. 1757-1773 (2012).
Non Patent Document 2: A. A. Freschi, et al, "Adjustable phase control in stabilized interferometry," OPTICS LETTERS, Vol. 20, No. 6, pp. 635-637 (1995).
Non Patent Document 3: Toyohiko Yamauchi, et al, "Low-coherent quantitative phase microscope for nanometer-scale measurement of living cells morphology," OPTICS EXPRESS, Vol. 16, No. 16, pp. 12227-12238 (2008).
Non Patent Document 4: Hidenao Iwai, et al, "Quantitative phase imaging using actively stabilized phase-shifting low-coherence interferometry," OPTICS LETTERS, Vol. 29, No. 20, pp. 3299-2401 (2004).
Non Patent Document 5: Ichirou Yamaguchi, et al, "Active phase-shifting interferometers for shape and deformation measurements," Opt. Eng., Vol. 35, No. 10, pp. 2930-2937 (1996).

SUMMARY OF INVENTION

Technical Problem

The interference observation apparatus disclosed in Non Patent Document 1 outputs the first split light or the second split light from the original optical path to the side once, sequentially reflects the light on two mirrors of which the reflecting surfaces are perpendicular to each other, and then returns the light to the original optical path. Then, the interference observation apparatus can change an optical path difference between the first split light and the second split light by moving the two mirrors. The interference observation apparatus having such a configuration is necessarily increased in size when the aperture of the optical system is increased to acquire an image having a high spatial resolution.

The present invention has been made in order to solve the above problem, and an object thereof is to provide an interference observation apparatus which has a function of adjusting the optical path difference using the optical system of the Mach-Zehnder interferometer, is able to acquire an image having a high spatial resolution, and is easily made small in size.

Solution to Problem

An interference observation apparatus according to one embodiment of the present invention includes (1) a light source for outputting incoherent light, and (2) an interference optical system forming a Mach-Zehnder interferometer and including a splitting beam splitter for splitting the light output from the light source to output first split light and second split light, and a combining beam splitter for combining the first split light and the second split light to output combined light. In the interference observation apparatus, the interference optical system includes a second beam splitter and a second mirror on an optical path of the second split light, causes the second beam splitter to transmit or reflect the second split light arrived at the second beam splitter from the splitting beam splitter and then causes the second mirror to reflect the second split light, causes the second beam splitter to reflect or transmit the second split light reflected by the second mirror and arrived at the second beam splitter, and outputs the second split light from the second beam splitter in a direction different from an input direction of the second split light from the splitting beam splitter to the second beam splitter. The second mirror freely moves in a direction perpendicular to a reflecting surface of the second mirror. Further, the interference optical system includes an optical element on an optical path of the first split light such that the total number of times of respective reflections of the first split light and the second split light is an even number.

Advantageous Effects of Invention

According to the present invention, an optical path difference can be adjusted using an optical system of the Mach-Zehnder interferometer, an image having a high spatial resolution is able to be acquired, and the apparatus is easily made small in size.

DESCRIPTION OF EMBODIMENTS

Hereinafter, embodiments for carrying out the present invention will be described in detail with reference to the accompanying drawings. In the description of the drawings, the same elements will be denoted by the same reference signs, without redundant description. The present invention is not limited to these examples, and the Claims, their equivalents, and all the changes within the scope are intended as would fall within the scope of the present invention.

First Embodiment

Figure 1:
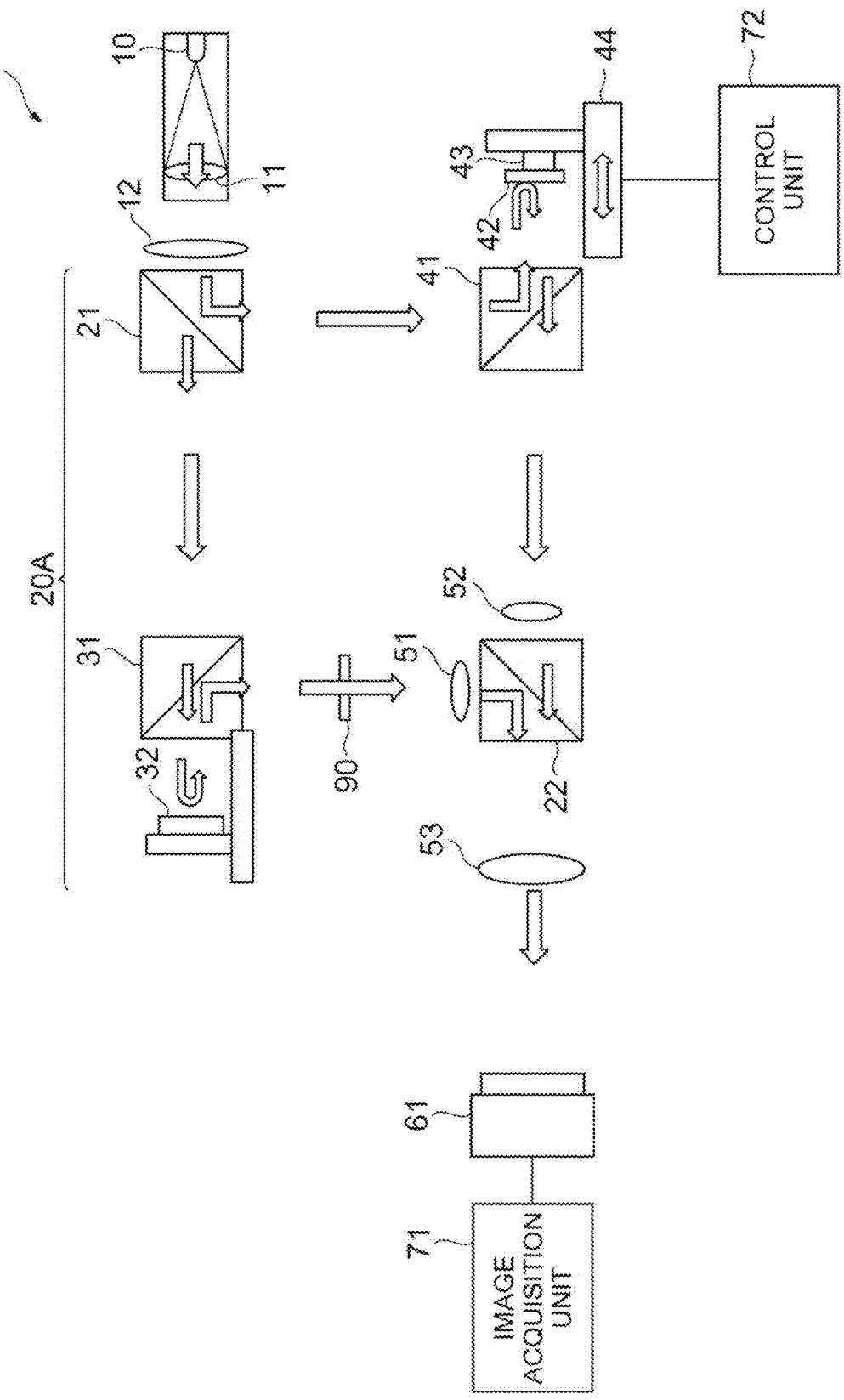
FIG. 1 is a diagram illustrating a configuration of an interference observation apparatus 1A of a first embodiment.

FIG. 1 is a diagram illustrating a configuration of an interference observation apparatus 1A of a first embodiment. The interference observation apparatus 1A includes a light source 10, a lens 11, a lens 12, a splitting beam splitter 21, a combining beam splitter 22, a beam splitter 31, a mirror 32, a beam splitter 41, a mirror 42, a piezo element 43, a stage 44, a lens 51, a lens 52, a tube lens 53, an imaging unit (light receiving unit) 61, an image acquisition unit 71, and a control unit 72. An interference optical system 20A from the splitting beam splitter 21 to the combining beam splitter 22 forms the Mach-Zehnder interferometer.

The interference observation apparatus 1A acquires an interference image on the basis of the light transmitted through an observation object 90. The observation object 90 is not limited to a specific cell or a biological sample. For example, the observation object includes a cultured cell, an immortalized cell, a primary cultured cell, a cancer cell, a fat cell, a liver cell, a cardiac muscle cell, a nerve cell, a glia cell, a somatic stein cell, an embryonic stem cell, a pluripotential stem cell, an iPS cell, and a cell aggregation (spheroid) created on the basis of at least one of these cells. Further, the observation object is not limited to a biological object, and includes an industrial sample which can be measured in the transmission type configuration, for example, an inner portion of glass, an inner portion of a semiconductor element, a resin material, a liquid crystal, a high molecular compound, and an optical element.

The light source 10 outputs incoherent light. The light source 10 may be, for example, a lamp light source such as a halogen lamp, an LED (Light emitting diode) light source, an SLD (Super luminescent diode) light source, or an ASE (Amplified spontaneous emission) light source, or the like. The lenses 11 and 12 condense the light output from the light source 10 to the observation object 90.

The splitting beam splitter 21 is optically coupled to the light source 10, inputs the light output from the light source 10 and passing through the lenses 11 and 12, and splits the light into two components to form first split light and second split light. The splitting beam splitter 21 may be a half mirror for example. The splitting beam splitter 21 outputs the first split light to the beam splitter 31 in an optical system on a measurement side, and outputs the second split light to the beam splitter 41 in an optical system on a reference side.

The beam splitter 31 and the mirror 32 are provided in the optical system on the measurement side. The beam splitter 31 inputs the first split light output from the splitting beam splitter 21 to reflect the light to the mirror 32, and inputs the first split light reflected by the mirror 32 to transmit the light to the combining beam splitter 22. The beam splitter 31 may be a half mirror for example.

The beam splitter 41, the mirror 42, the piezo element 43, and the stage 44 are provided in the optical system on the reference side. The beam splitter 41 inputs the second split light output from the splitting beam splitter 21 to reflect the light to the mirror 42, and inputs the second split light reflected by the mirror 42 to transmit the light to the combining beam splitter 22. The beam splitter 41 may be a half mirror for example.

The piezo element 43 can move the mirror 42 in a direction perpendicular to a reflecting surface of the mirror 42. The stage 44 can move the mirror 42 and the piezo element 43 in the direction perpendicular to the reflecting surface of the mirror 42. The piezo element 43 and the stage 44 can adjust the optical path length of the optical system on the reference side, and can adjust an optical path difference between the first split light and the second split light. The stage 44 can roughly adjust the optical path difference, and the piezo element 43 can finely adjust the optical path difference.

The combining beam splitter 22 inputs the first split light output from the beam splitter 31 and passing through the observation object 90 and the lens 51, inputs the second split light output from the beam splitter 41 and passing through the lens 52, and combines the first split light and the second split light to output combined light. The combining beam splitter 22 may be a half mirror for example.

The tube lens 53 guides the combined light output from the combining beam splitter 22 to the imaging unit 61, and forms an image of the combined light on an imaging plane of the imaging unit 61. The imaging unit 61 receives the combined light and outputs a detection signal, and in particular, outputs the detection signal indicating an intensity distribution of the combined light on the imaging plane. The imaging unit 61 is, for example, an image sensor such as a CCD area image sensor or a CMOS area image sensor.

The image acquisition unit 71 inputs the detection signal output from the imaging unit 61, and acquires the interference image of the observation object 90 on the basis of the detection signal. The image acquisition unit 71 may be configured by an image processing processor such as an FPGA (field-programmable gate array) or a GPU (Graphics Processing Unit), or may be a computer such as a personal computer or a tablet terminal. Further, the image acquisition unit 71 may include a display unit for displaying the interference image and the like.

The control unit (controller) 72 drives both or any one of the piezo element 43 and the stage 44 to move the mirror 42, and adjusts the optical path length of the optical system on the reference side. With this configuration, the control unit 72 can adjust a phase difference between the first split light and the second split light at the time of the combining by the combining beam splitter 22.

Here, each of the image acquisition unit 71 and the control unit 72 is a computer which includes a processor and a memory. Further, the image acquisition unit 71 and the control unit 72 may be configured by individual computers, or may be configured by one computer. The computer may be, for example, a personal computer or a smart device such as a tablet terminal. Further, the image acquisition unit 71 or the control unit 72 may include an input unit (keyboard, mouse, tablet terminal, etc.) which receives an input from a user, and a display unit (display, tablet terminal, speaker, vibrator) which displays an interference intensity, etc. Further, in a case where the display unit can display a screen such as the display or the tablet terminal, the interference image etc. may be displayed with the interference intensity.

The interference image of the observation object 90 can be acquired using the interference observation apparatus 1A as described below. The incoherent light output from the light source 10 passes through the lenses 11 and 12, and is split by the splitting beam splitter 21 into two components to be the first split light and the second split light. The first split light output from the splitting beam splitter 21 transmits the beam splitter 31, and is reflected by the mirror 32. The first split light reflected by the mirror 32 is reflected by the beam splitter 31, is condensed on the observation object 90, and transmits the observation object 90. The first split light transmitting the observation object 90 passes through the lens 51 and is input to the combining beam splitter 22. The first split light is optically delayed when transmitting the observation object 90. The second split light output from the splitting beam splitter 21 is reflected by the beam splitter 41, and reflected by the mirror 42. The second split light reflected by the mirror 42 transmits the beam splitter 41, and is input to the combining beam splitter 22 through the lens 52.

The first split light input from the lens 51 to the combining beam splitter 22 and the second split light input from the lens 52 to the combining beam splitter 22 are combined by the combining beam splitter 22. The combined light passes through the tube lens 53, and is received by the imaging unit 61. The image acquisition unit 71 acquires the interference image on the basis of the detection signal output from the imaging unit 61 which receives the combined light. Further, the position of the mirror 42 is controlled by the piezo element 43 or the stage 44 which is driven by the control unit 72, and thus the optical path difference between the first split light and the second split light is adjusted, and the phase difference between the first split light and the second split light at the time of the combining by the combining beam splitter 22 is adjusted.

In particular, in the present embodiment, the beam splitter 31 and the mirror 32 are provided on the optical path of the first split light in the interference optical system 20A. The first split light arrived at the beam splitter 31 from the splitting beam splitter 21 transmits the beam splitter 31, and then is reflected by the mirror 32. The first split light reflected by the mirror 32 is reflected by the beam splitter 31, and output from the beam splitter 31 in a direction different from the input direction of the first split light from the splitting beam splitter 21 to the beam splitter 31.

Further, the beam splitter 41 and the mirror 42 are provided on the optical path of the second split light in the interference optical system 20A. The second split light arrived at the beam splitter 41 from the splitting beam splitter 21 is reflected by the beam splitter 41, and then reflected by the mirror 42. The second split light reflected by the mirror 42 transmits the beam splitter 41, and is output from the beam splitter 41 in a direction different from the input direction of the second split light from the splitting beam splitter 21 to the beam splitter 41.

The mirror 42 moves in a direction perpendicular to the reflecting surface by both or any one of the piezo element 43 and the stage 44 which are driven by the control unit 72. The optical path difference between the first split light and the second split light is adjusted by the movement of the mirror 42.

Here, there may be provided a piezo element which can move the mirror 32 in a direction perpendicular to a reflecting surface of the mirror 32. Further, there may be provided a stage which can move the mirror 32 and the piezo element in the direction perpendicular to the reflecting surface of the mirror 32.

In the interference optical system 20A, the first split light is reflected by the beam splitter 31 and the mirror 32, and thus the image is reversed twice. Further, the second split light is reflected by the beam splitter 41 and the mirror 42, and thus the image is similarly reversed twice. As a result, the respective images of the first split light and the second split light at the time of combining by the combining beam splitter 22 are matched with each other in direction. The beam splitter 31 and the mirror 32 or the beam splitter 41 and the mirror 42 are optical elements provided such that the total number of times of respective reflections of the first split light and the second split light is an even number.

In general, when the total number of times of image inversions by the respective reflections of the first split light and the second split light is an even number, the respective images of the first split light and the second split light are matched with each other in direction at the time of the combining by the combining beam splitter 22. When the respective images of the first split light and the second split light at the time of the combining by the combining beam splitter 22 are matched with each other in direction, the first split light and the second split light can interfere efficiently in a wide range of the imaging plane of the imaging unit 61.

In a case where a temporally incoherent light source is used as the light source 10, there is a need to set the optical path difference between the first split light and the second split light in the interference optical system 20A to be the coherent length or less of the light in order to make interference fringes of the combined light formed by combining the first split light and the second split light by the combining beam splitter 22 be observed on the imaging plane of the imaging unit 61. Since the first split light transmits the observation object 90 which is disposed in the vicinity of the front focal plane of the lens 51, there occurs an optical delay by the transmission. The observation object 90 is, for example, a cell in a culture solution. The culture solution has a different component according to the cell which is the observation object, and when the component is different, the refractive index is also different. Further, since there is an influence such as a manufacturing error, it cannot be said that the thickness of a sample chamber is fixed. On the other hand, the second split light may be adjusted in its optical path length according to the position of the mirror 42. In the present embodiment, the optical path difference between the first split light and the second split light can be made the coherent length or less of the light by appropriately adjusting the position of the mirror 42 by the control unit 72 for each observation object, and thus, the interference image of the observation object can be acquired.

Further, in the present embodiment, a light source (halogen lamp, LED, or the like) which outputs spatially incoherent diffused light may be used as the light source 10. That is, in the interference observation apparatus 1A, all the optical elements from the light source 10 to the lenses 51 and 52 can have sufficiently large apertures (for example, 10 mm or more) compared to the beam diameter at the time when the light source 10 outputs the light, and therefore, incoherent illumination (that is, high NA illumination) can be made using the spatially incoherent light. The output light of the light source 10 can be condensed in the vicinity of the front focal planes of the lenses 51 and 52 by the two lenses 11 and 12 provided between the light source 10 and the splitting beam splitter 21, so that the output light of the light source 10 can be used with high efficiency, and the high NA illumination can be realized.

Figure 2:
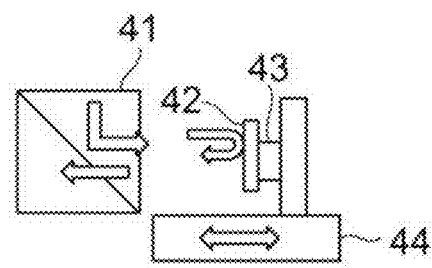
FIG. 2 includes diagrams for comparing to describe an optical path length adjusting mechanism in the present embodiment and an optical path length adjusting mechanism of a comparative example.
Figure 2:
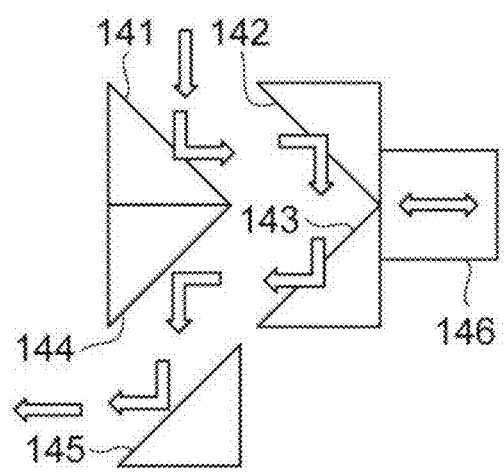

FIG. 2 includes diagrams for comparing to describe an optical path length adjusting mechanism in the present embodiment and an optical path length adjusting mechanism in a comparative example. In the optical path length adjusting mechanism of the comparative example illustrated in (b) in FIG. 2, the light is sequentially reflected by mirrors 141 to 145, and the positions of the mirrors 142 and 143 are adjusted by a stage 146 to adjust the optical path length. In the optical path length adjusting mechanism of the comparative example, in a case where a large aperture is realized, a lot of optical elements are necessary, and a large size optical system is required. For this reason, the optical path length from the splitting beam splitter to the combining beam splitter becomes long in the optical path length adjusting mechanism of the comparative example, and therefore, there is a problem in that the NA of the illumination system cannot be made high, and the optical system becomes weak against disturbance such as vibrations.

On the other hand, in the optical path length adjusting mechanism in the present embodiment illustrated in (a) in FIG. 2, the required number of optical elements can be reduced, and the size of the optical system can be made small. For this reason, in the optical path length adjusting mechanism in the present embodiment, the optical path length from the splitting beam splitter to the combining beam splitter can be made short, so that the NA of the illumination system can be made high, and it is possible to suppress the weakness of the optical system against the disturbance such as vibrations.

Figure 10:
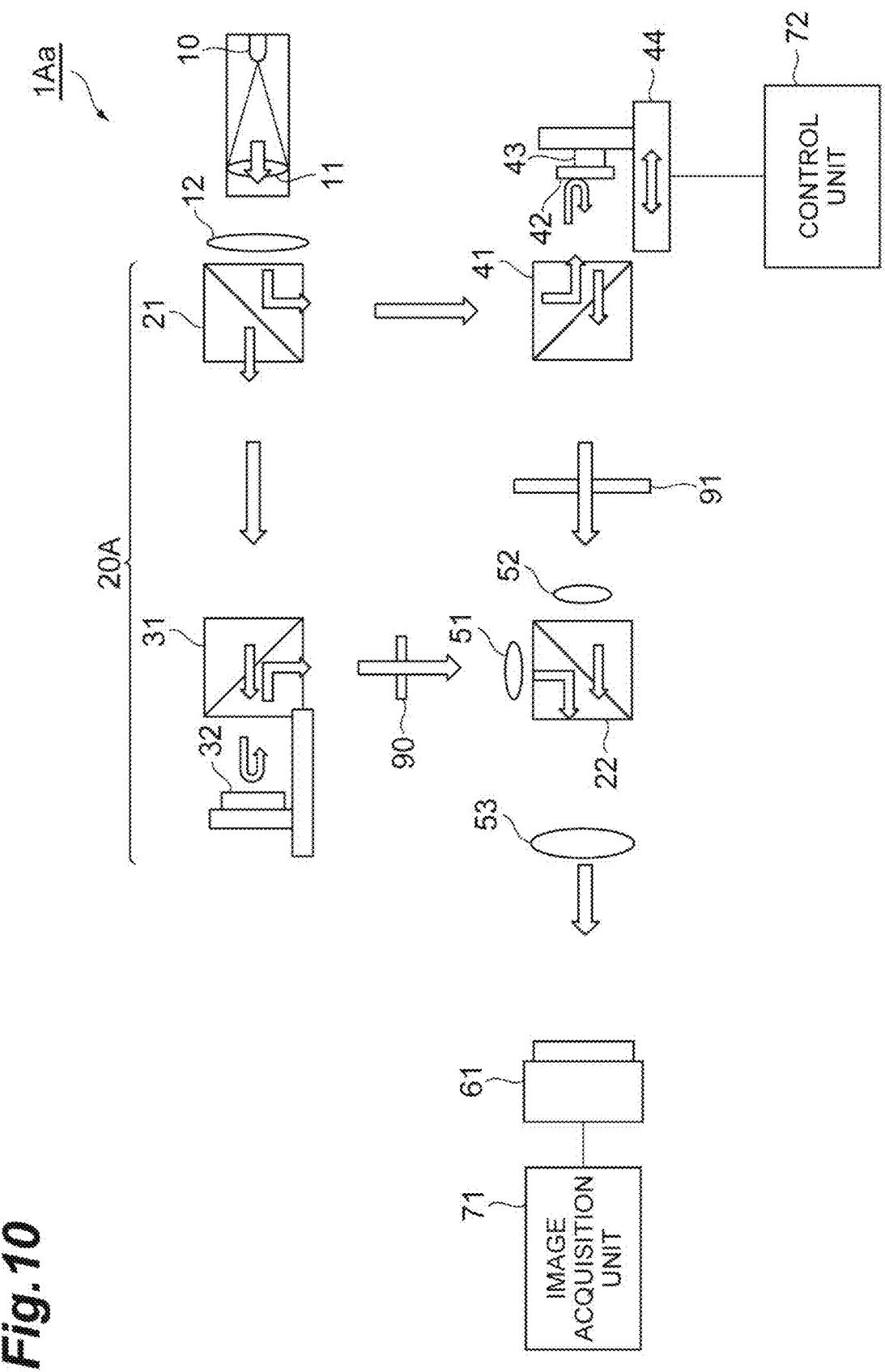
FIG. 10 is a diagram illustrating a configuration of an interference observation apparatus 1Aa of a modification of the first embodiment.
Figure 11:
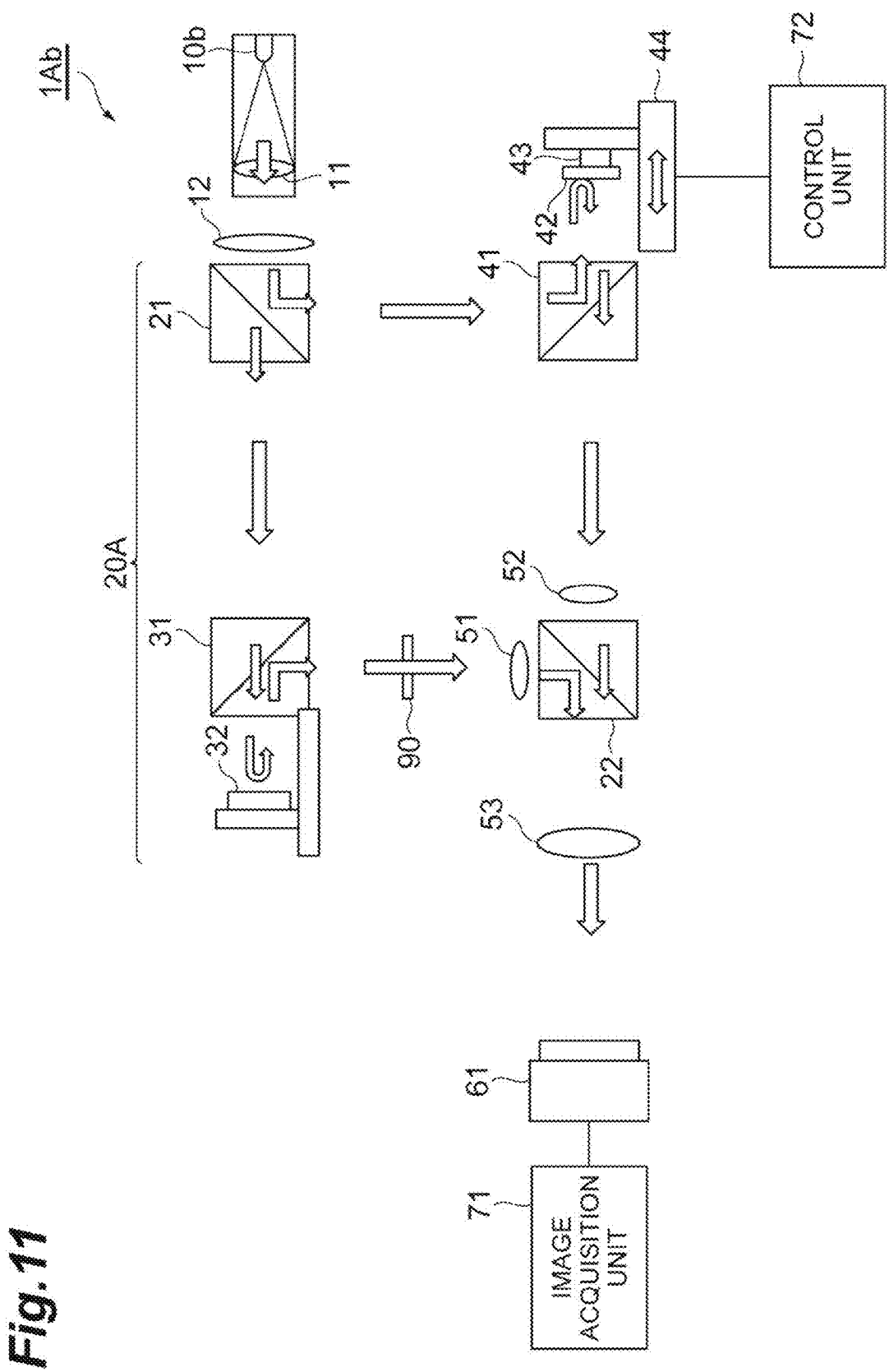
FIG. 11 is a diagram illustrating a configuration of an interference observation apparatus 1Ab of a modification of the first embodiment.
Figure 12:
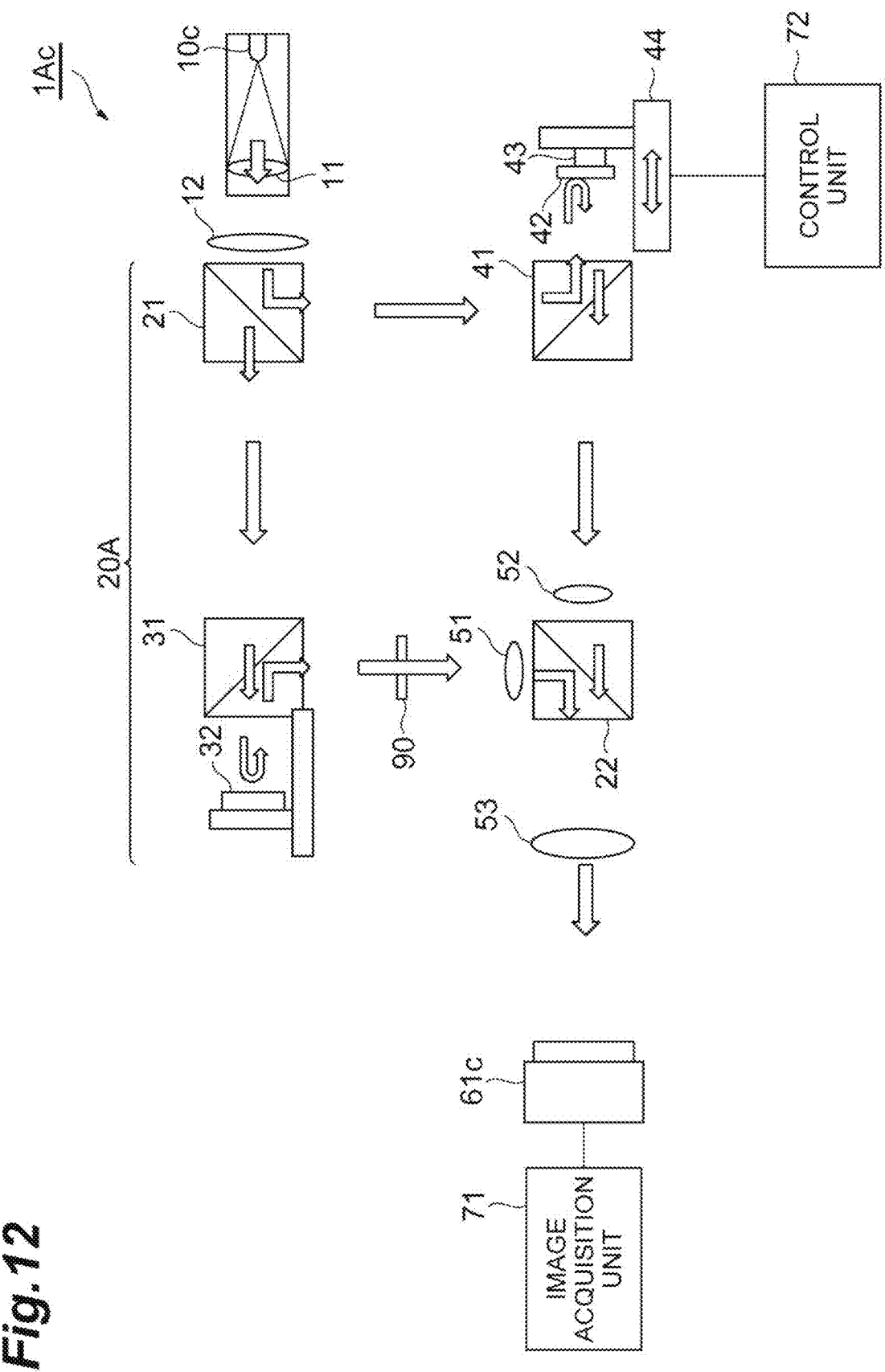
FIG. 12 is a diagram illustrating a configuration of an interference observation apparatus 1Ac of a modification of the first embodiment.

As modifications of the first embodiment, the configurations of the interference observation apparatuses 1Aa, 1Ab, and 1Ac illustrated in FIG. 10 to FIG. 12 can be taken into consideration.

In the configuration of the interference observation apparatus 1B, when the sample 90 is replaced with another sample, the thickness or the refractive index of the sample changes, and thus there may occur a need to move the stage 44 over a long distance. For example, in a case where a cover glass having a thickness of 170 μm is used as a sample, and 1.5 is assumed as a refractive index of glass, an increment of the optical path length generated in a case where there is a sample is 85 μm (=170×(1.5−1)) compared to a case where there is no sample. On the other hand, in a case where a plastic dish having a bottom thickness of 1 mm filled with water by a depth of 3 mm is used as the sample, 1.7 is assumed as a refractive index of plastic, and 1.33 is assumed as a refractive index of water, an increment of the optical path length generated in a case where there is a sample becomes 1690 μm (=1000×(1.7−1)+3000×(1.33−1)) compared to a case where there is no sample. Therefore, in a case where the sample is changed from the cover glass to the plastic dish filled with water, an extra optical path difference of 1605 μm is generated. The stage 44 is necessarily moved by 802.5 μm in a direction of elongating the optical path length in order to compensate the optical path difference and to obtain an optical path difference which maximizes an interference degree with the same order as that before changing the sample. The movement of the stage by nearly 1 mm may cause a reduction of operability in a case where a manual stage is used for example, or there is a need to use a heavy stepping motor stage in a case where an automatic stage is used.

Therefore, as a method for reducing the movement amount of the stage 44, it is possible to consider a configuration of an interference observation apparatus 1Aa illustrated in FIG. 10 as a modification of the first embodiment. FIG. 10 is a diagram illustrating the configuration of the interference observation apparatus 1Aa of the modification of the first embodiment. The interference observation apparatus 1Aa includes an optical path length/dispersion compensating plate 91 on the optical system on the reference side in addition to the configuration of the interference observation apparatus 1A.

The optical path length/dispersion compensating plate 91 is formed to have almost the same optical path length using almost the same material as that of the using sample, in accordance with the variation of samples that the user uses, and transmits the light. For example, in a case where the user uses the samples on which an object is coated or cultured on three types of holders, that is, a cover glass having a thickness of 170 a slide glass having a thickness of 1 mm, and a container filled with water by a depth of 3 mm on a plastic dish having a bottom thickness of 1 mm, an optical path length/dispersion compensating plate A (for the cover glass), an optical path length/dispersion compensating plate B (for the slide glass), and an optical path length/dispersion compensating plate C (for the container filled with water on the plastic dish) may be prepared in advance as plates through which the light having the same optical path length as those of the holders transmits.

The optical path length/dispersion compensating plates A to C are prepared in advanced, and for example, the optical path length/dispersion compensating plate A is inserted at an arbitrary position in a reference optical path in a case where the cover glass having a thickness of 170 μm is the holder, the optical path length/dispersion compensating plate B in a case where the slide glass having a thickness of 1 mm is the holder, and the optical path length/dispersion compensating plate C in a case where the container filled with water by a depth of 3 mm on the plastic dish having a bottom thickness of 1 mm is the holder, and therefore, even after the sample is changed, it is possible to obtain the optical path difference to maximize the interference degree similarly to that before the changing with the same order as that before the changing.

Here, even in a case where almost the same sample, for example, a commercially available cover glass having a nominal thickness of 170 μm, is used, it is not necessarily realized an optical path difference in which the interference degree is maximized only by inserting the optical path length/dispersion compensating plate 91 depending on a refractive index difference of a material due to a condition such as a manufacturing error and a temperature. For example, the cover glass having a nominal thickness of 170 μm may have a manufacturing error of ±10 μm. Further, in the case of the holder filled with water or a culture solution on the plastic dish, a measurement object such as a cell is observed in a state where the object is cultured on the bottom of the dish in practice, and therefore, the value of the optical path length varies depending on a thickness of the cell and a composition of the culture solution. Therefore, even in a case where the optical path length/dispersion compensating plate 91 is used, it does not mean that the stage 44 or a mechanical optical path difference adjusting mechanism similar to the stage is unnecessary.

In a case where the optical path length/dispersion compensating plate 91 is used, and a manual stage is used as the stage 44, the stage using a differential micrometer can be preferably used. The differential micrometer is a micrometer formed by integrating two adjusting mechanisms of a rough motion (a long distance can be moved, but a resolution is low) and a fine motion (only a short distance can be moved, but a resolution is high). At the time of factory shipment, the optical path difference is set to almost zero by the rough motion stage without a sample, and the rough motion stage is fixed. At the time of observation, the user inserts the optical path length/dispersion compensating plate 91 corresponding to the optical path length of the measurement sample, and after setting the optical path difference to almost zero, the optical path difference is set to strictly zero using only the fine motion stage, and thus, it is possible to obtain the interference of the incoherent light. In the present embodiment, since the user operates only the fine motion stage, the adjustment range is narrow compared to a case where the rough motion stage is used, and there is a less possibility to miss a point at which the optical path difference becomes zero.

In a case where the optical path length/dispersion compensating plate 91 is used, and an automatic stage is used as the stage 44, it is preferably possible to use the stage in which the piezo element is used. The piezo element has an extension distance of about 100 µm in maximum. At the time of factory shipment, the optical path difference is designed and manufactured to be almost zero in a state where there is no sample. At the time of observation, the user inserts the optical path length/dispersion compensating plate 91 corresponding to the optical path length of the measurement sample, and after setting the optical path difference to almost zero, the optical path difference is set to strictly zero using the stage 44 with the piezo element, and thus, it is possible to obtain the interference of the incoherent light. Further, in the case of the present embodiment, the piezo element 43 may be not necessary, and the function of the present invention may be realized only by the stage 44 using the piezo element.

Here, in the explanation of the present example, the reason why the plate for correcting the optical path difference is called "optical path length/dispersion compensating plate" is that not only the optical path length but also an influence caused by dispersion in various samples can be compensated by inserting this optical plate. In the two-beam interferometer, not only the optical path lengths of an object optical path and the reference optical path but also the dispersions (=wavelength dependency of the optical path length) are also equalized, so that it is possible to achieve the highest visibility of the interference fringes. As a secondary effect obtained by using the optical path length/dispersion compensating plate 91 in accordance with the type of the sample, the imaging can be performed in a state where the interference fringe has the high visibility.

Further, the optical path length/dispersion compensating plate 91 can exert the effect by being inserted at an arbitrary position in the reference optical path, and preferably inserted in the vicinity of the focal point on the light source side of the lens 52 on the reference side, so that it is possible to reduce a wavefront aberration between the reference light and the object light. Further, more preferably, the insertion position of the optical path length/dispersion compensating plate 91 is in the vicinity of the focal point on the light source side of the lens 52 in the optical system on the reference side, and further, it is inserted at a position deviated toward the light source side or the imaging unit side by several mm from the strict focal position (about several times the focal depth of the lens 52), so that it is possible to avoid that dust or the like in the surface of the optical path length/dispersion compensating plate 91 is reflected on the imaging plane of the imaging unit 61. Further, in a case where the optical path length/dispersion compensating plate 91 is inserted into a turning portion for the adjustment of the optical path length (between the beam splitter 41 and the mirror 42), the reference light is transmitted twice through the optical path length/dispersion compensating plate 91, and therefore, it is desirable to use the optical path length/dispersion compensating plate 91 which is manufactured to have the half of the optical thickness of the measurement sample.

The configuration using the optical path length/dispersion compensating plate 91 can be implemented not only in the modification of the first embodiment but also in the modifications of the second to fifth embodiments described below.

Further, as a modification of the first embodiment, it is possible to consider a configuration in which a wavelength dispersion of the measurement sample is imaged as a configuration of an interference observation apparatus 1Ab illustrated in FIG. 11. In the present embodiment, an incoherent wavelength-variable light source 10b, for example, the light source device of model No. L12194 made by Hamamatsu Photonics, is used as the light source. In the present embodiment, the stage 44 is adjusted such that the optical path difference becomes zero in the beginning using the white light having a broadband containing almost all the bands used in measurement, and then the imaging is performed using the wavelength-variable light source 10b in place of the light source. In the measurement, the wavelength of the light source 10b is changed in plural times to obtain a phase image of the measurement sample (=optical thickness distribution). Through such a measurement, the wavelength dispersion of the measurement sample can be obtained.

In a case where the sample having no wavelength dispersion has a thickness of L and a specific refractive index of $\Delta n$, the optical thickness OT of the sample is $OT = L \times \Delta n$ which is constant regardless of the wavelength. When the phase difference observed in the sample is set to $\Delta \phi$, the optical thickness OT can be easily calculated as $OT = \lambda \times \Delta \phi / (2\pi)$. On the other hand, in a sample having a wavelength dispersion, the specific refractive index of the sample is expressed in a function of wavelength, and therefore, the optical thickness OT of the sample becomes $OT = L \times \Delta n(\lambda)$, and has the wavelength dependency.

The center wavelength of the output light of the light source 10b is changed to $\lambda_1, \lambda_2, \lambda_3, \ldots \lambda_N$ to acquire a quantitative phase image, so that phase difference images $\Delta \phi_1, \Delta \phi_2, \Delta \phi_3, \ldots, \Delta \phi_N$ of the light transmitting the sample can be sequentially acquired. On the basis of these images, the optical thicknesses $OT_1, OT_2, \ldots, OT_N$ in the respective wavelengths can also be calculated as $OT_n = \lambda_n \times \Delta \phi_n / (2\pi)$. Here, when $\Delta n_{ratio}(\lambda_n) = OT_n / OT_1$ is introduced as the wavelength dependency of the refractive index difference, $\Delta n_{ratio}(\lambda_n) = \Delta n(\lambda_n) / \Delta n(\lambda_1)$ is obtained, and therefore, it can be seen that this value is a unique value of the material of the sample regardless of the thickness L of the sample.

Since the wavelength dependency of the refractive index is known for various materials, the material of the measurement sample can be identified on the basis of the wavelength dependency of the refractive index difference obtained by the above method. Alternatively, for a new material of which the wavelength dependency of the refractive index is not known, the wavelength dependency of the refractive index of the material can be obtained on the basis of the wavelength dependency of the refractive index difference obtained by the above method.

Further, a configuration of an interference observation apparatus 1Ac illustrated in FIG. 12 may be considered. In the configuration of the interference observation apparatus 1Ac, a color-type imaging unit 61c is used instead of using a multiwavelength light source as the light source, and an incoherent white light source 10c having a wide band is used as the light source. The incoherent white light source 10c having a wide band is preferably a halogen lamp or a white LED. The color-type imaging unit 61c is preferably a color CCD camera or a color CMOS camera in which a color filter is attached to the imaging plane, or a multispectral camera in which a switchable color filter is used in the front face of the CCD camera. Even in this configuration, the quantitative phase images of the respective sensitivity wavelengths $\lambda_1$, $\lambda_2$, $\lambda_3$, . . . , $\lambda_N$ of the camera are acquired, so that the wavelength dependency of the refractive index difference described above can be obtained. With this configuration, the material of the measurement sample can be identified, or the wavelength dependency of the refractive index of the material of a new material having unknown wavelength dependency of the refractive index can be obtained.

The configuration of imaging the wavelength dispersion of the measurement sample can be implemented not only as the modification of the first embodiment but also as modifications of the second to fifth embodiments described below.

Second Embodiment

Figure 3:
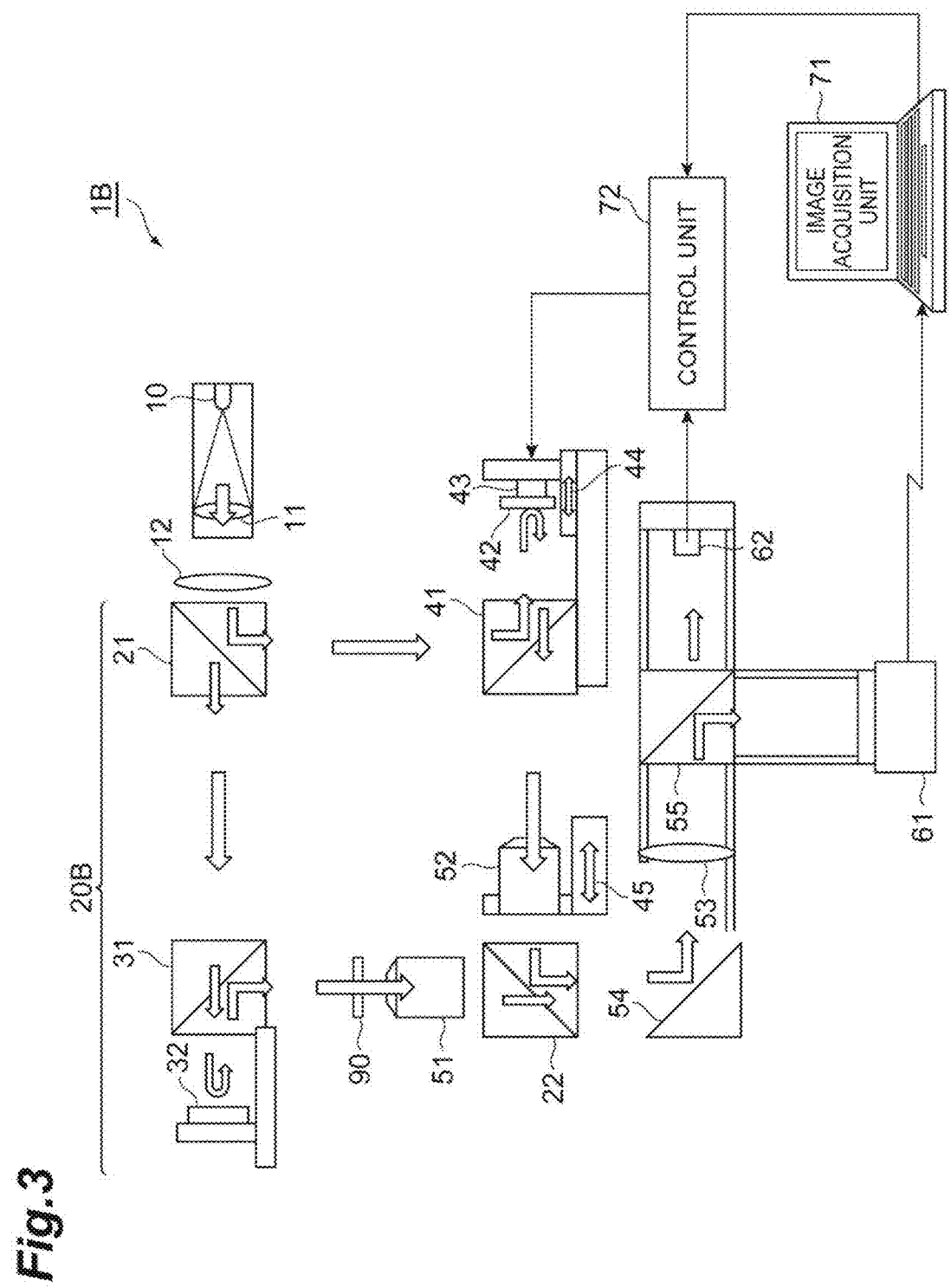
FIG. 3 is a diagram illustrating a configuration of an interference observation apparatus 1B of a second embodiment.

FIG. 3 is a diagram illustrating a configuration of an interference observation apparatus 1B of a second embodiment. The interference observation apparatus 1B includes a light source 10, a lens 11, a lens 12, a splitting beam splitter 21, a combining beam splitter 22, a beam splitter 31, a mirror 32, a beam splitter 41, a mirror 42, a piezo element 43, a stage 44, a stage 45, a lens 51, a lens 52, a tube lens 53, a mirror 54, a beam splitter 55, an imaging unit (light receiving unit) 61, a photodetector (light receiving unit) 62, an image acquisition unit 71, and a control unit 72. An interference optical system 20B from the splitting beam splitter 21 to the combining beam splitter 22 forms the Mach-Zehnder interferometer.

The interference observation apparatus 1B of the second embodiment illustrated in FIG. 3 is different from the configuration of the interference observation apparatus 1A of the first embodiment illustrated in FIG. 1 in that there are further provided the stage 45, the mirror 54, the beam splitter 55, and the photodetector (light receiving unit) 62.

The stage 45 moves the lens 52 in a direction of the optical axis of the lens 52 which is provided on the optical path of the second split light between the beam splitter 41 and the combining beam splitter 22.

The tube lens 53 causes the combined light output from the combining beam splitter 22 and reflected by the mirror 54 to form an image on the imaging plane of the imaging unit 61 through the beam splitter 55. The beam splitter 55 is a splitting unit which splits the light arrived from the combining beam splitter 22 through the tube lens 53, outputs one split light (first detection light) to the imaging unit 61, and outputs the other split light (second detection light) to the photodetector 62.

The light receiving unit which receives the combined light and outputs the detection signal includes the imaging unit 61 and the photodetector 62. The imaging unit 61 receives the first detection light arrived from the beam splitter 55 and outputs the received light signal (first detection signal). The imaging unit 61 is, for example, an image sensor such as a CCD area image sensor or a CMOS area image sensor. The photodetector 62 receives the second detection light arrived from the beam splitter 55 and outputs the received light signal (second detection signal). The photodetector 62 is, for example, a photodiode, an avalanche photodiode, a photomultiplier tube, a line sensor (linear sensor), a CCD area image sensor, or a CMOS area image sensor. The image acquisition unit 71 acquires the interference image on the basis of the first detection signal output from the imaging unit 61. The control unit 72 performs control on the basis of the second detection signal output from the photodetector 62.

The interference image of the observation object 90 can be acquired using the interference observation apparatus 1B as described below. The incoherent light output from the light source 10 passes through the lenses 11 and 12, and is split by the splitting beam splitter 21 into two components to be the first split light and the second split light. The first split light output from the splitting beam splitter 21 transmits the beam splitter 31, and is reflected by the mirror 32. The first split light reflected by the mirror 32 is reflected by the beam splitter 31, is condensed on the observation object 90, and transmits the observation object 90. The first split light transmitting the observation object 90 passes through the lens 51 and is input to the combining beam splitter 22. The first split light is optically delayed when transmitting the observation object 90. The second split light output from the splitting beam splitter 21 is reflected by the beam splitter 41, and reflected by the mirror 42. The second split light reflected by the mirror 42 transmits the beam splitter 41, and is input to the combining beam splitter 22 through the lens 52.

The first split light input from the lens Si to the combining beam splitter 22 and the second split light input from the lens 52 to the combining beam splitter 22 are combined by the combining beam splitter 22. The combined light passes through the mirror 54 and the tube lens 53, is split by the beam splitter 55 into two components, is received by the imaging unit 61, and is received by the photodetector 62. The image acquisition unit 71 acquires the interference image on the basis of the first detection signal output from the imaging unit 61 which receives the combined light. Further, the control unit 72 controls the optical path difference adjusting operation of the optical path difference adjusting mechanism (the piezo element 43, the stage 44) on the basis of the second detection signal output from the photodetector 62 which receives the combined light.

In the present embodiment, a deviation of the phase difference generated by disturbance in the optical system is detected, the control unit 72 performs a phase lock and a phase shift by controlling the position of the mirror 42, and the interference image and the phase image of the observation object 90 are acquired. Here, a technique of keeping the phase difference between the first split light and the second split light at the time of the combining is called "phase lock", and further, a technique of changing a value of the optical path difference kept by the phase lock using the feedback control is called "phase shift". Further, the disturbance described herein includes not only mechanical vibrations of the optical system but also the deviation of the optical path length caused by the vibration of a boundary between the liquid surface and the air in a case where the observation object 90 is a cell in a liquid. The control by the control unit 72 will be described in detail below.

In the present embodiment, since the interference image is acquired using the incoherent light output by the light source 10, there is a need to perform a phase lock and a phase shift by controlling the optical path difference. This is because, in the case of the incoherent light, that is, white light, the interference is obtained in a case where the optical path difference is a coherence length $\Delta L_C$ or less. When a center wavelength of the incoherent light is set to $\lambda_0$, and a spectrum width of the incoherent light is set to $\Delta\lambda$, the coherence length $\Delta L_C$ is expressed by the following Formula (1). In the case of an LED, the coherence length $\Delta L_C$ is about 10 μm. In the case of a halogen lamp, the coherence length $\Delta L_C$ is about 1 μm.

[Formula 1]

$$\Delta L_C = 2 \times 0.441 \frac{\lambda_0^2}{\Delta\lambda} \qquad (1)$$

As the phase lock, a technique disclosed in Non Patent Documents 2, 3, and 4 may be used (hereinafter, referred to as "first phase lock technique"). In the phase lock technique disclosed in these Non Patent Documents, the mirror 42 is caused to vibrate at a high speed in a sinusoidal manner with a sufficiently small amplitude compared to the wavelength of the output light of the light source 10, and at this time, the detection signal output from the photodetector 62 is detected in synchronization with one time and two times the vibration frequency of the mirror 42, to obtain the phase of the interference light. The control unit 72 performs feedback control to make the obtained phase value approach a target value, so that the phase difference can be locked.

The control unit 72 inputs the detection signal which is an analog signal from the photodetector 62, and outputs an analog signal for the drive control of the piezo element 43 or the stage 44. The control unit 72 may perform an analog process internally, or a digital process. In the latter case, for example, the control unit 72 may perform an AD conversion on the input detection signal into a digital signal, process the digital signal, perform a DA conversion on the digital signal obtained by the processing to obtain an analog signal, and output the analog signal. In processing the digital signal, a microprocessor or an FPGA (Field Programmable Gate Array) may be used.

When the phase difference between the first split light and the second split light at the time of the combining is $\Delta\phi$, an intensity V of the light received by the photodetector 62 is expressed by the following Formula (2). The light receiving intensity V includes an offset component DC and an amplitude AC which are all unknown. Therefore, there is a need to extract the phase difference $\Delta\phi$ where the DC and the AC are not contained by a certain process.

[Formula 2]

$$V = DC + AC \cdot \sin(\Delta\phi) \qquad (2)$$

When the mirror 42 is caused to vibrate at a high speed in a sinusoidal manner by the piezo element 43 with a sufficiently small amplitude compared to the wavelength of the output light of the light source 10, the intensity V of the light received by the photodetector 62 is expressed by the following Formula (3). α is a modulation degree which is determined according to an amplitude of the vibration of the mirror 42. ω is an angular frequency of the vibration. t is a time variable.

[Formula 3]

$$V(t) = DC + AC \cdot \sin(\Delta\phi + \alpha \cdot \sin(\omega t)) \qquad (3)$$

When the right side of Formula (3) is expanded in a Fourier series, the following Formula (4) is obtained as an approximation formula. $J_1$ and $J_2$ are Bessel functions of the first kind. The second term in the right side of Formula (4a) vibrates at an amplitude $A_{\omega t}$ and an angular frequency ω. Further, the third term in the right side of Formula (4a) vibrates at an amplitude $A_{2\omega t}$ and an angular frequency 2ω. Therefore, the detection signal output from the photodetector 62 is synchronously detected with the angular frequency ω to obtain the amplitude $A_{\omega t}$, and the detection signal is synchronously detected with the angular frequency 2ω to obtain the amplitude $A_{2\omega t}$.

[Formula 4]

$$V(t) = DC' + A_{\omega t}\sin(\omega t) + A_{2\omega t}\cos(2\omega t) + \ldots \qquad (4a)$$

$$A_{\omega t} = 2 \cdot AC \cdot J_1(\alpha) \cdot \cos(\Delta\phi) \qquad (4b)$$

$$A_{2\omega t} = 2 \cdot AC \cdot J_2(\alpha) \cdot \sin(\Delta\phi) \qquad (4c)$$

A ratio of the amplitude $A_{\omega t}$ and the amplitude $A_{2\omega 7}$ is expressed by the following Formula (5). Further, the AC indicates the interference intensity of the combined light, and the interference intensity AC is expressed by the following Formula (6). Since the amplitude of the vibration of the mirror 42 is constant, $J_1(\alpha)$ and $J_2(\alpha)$ can be obtained on the basis of the amplitude. The phase difference $\Delta\phi$ in accordance with the optical path difference can be obtained on the basis of Formula (5), and the interference intensity AC can be obtained on the basis of Formula (6). The control unit 72 includes a synchronous detection circuit, an adding circuit, and a multiplying and dividing circuit for performing the above processes.

[Formula 5]

$$\frac{A_{2\omega t}}{A_{\omega t}} = \frac{2 \cdot AC \cdot J_2(\alpha) \cdot \sin(\Delta\phi)}{2 \cdot AC \cdot J_1(\alpha) \cdot \cos(\Delta\phi)} = \frac{J_2(\alpha)}{J_1(\alpha)}\tan(\Delta\phi) \qquad (5)$$

[Formula 6]

$$AC^2 = \left(\frac{A_{\omega t}}{2 \cdot J_1(\alpha)}\right)^2 + \left(\frac{A_{2\omega t}}{2 \cdot J_2(\alpha)}\right)^2 \qquad (6)$$

The phase lock technique (hereinafter, referred to as "second phase lock technique") using a "spatial filtering detector" disclosed in Non Patent Document 5 can also be used. In this technique, a line sensor having a plurality of pixels arranged in one-dimensional direction or a plurality of photodetectors arranged in one-dimensional direction is used in place of the photodetector 62. In the following, the description will be given about a case where four photodetectors arranged at equal intervals are used. An inclination is given to both or any one of the optical system on the measurement side and the optical system on the reference side to make interference fringes appear, and in this state, the inclination of the interference fringes is adjusted to set the light receiving intensities $V_1$ to $V_4$ of the four photodetectors to be obtained as the following Formula (7).

[Formula 7]

$$V_1 = DC + AC \cdot \sin(\Delta\phi) \quad (7a)$$

$$V_2 = DC + AC \cdot \sin(\Delta\phi + \pi/2) = DC - AC \cdot \cos(\Delta\phi) \quad (7b)$$

$$V_3 = DC + AC \cdot \sin(\Delta\phi + \pi) = DC - AC \cdot \sin(\Delta\phi) \quad (7c)$$

$$V_4 = DC + AC \cdot \sin(\Delta\phi + 3\pi/2) = DC + AC \cdot \cos(\Delta\phi) \quad (7d)$$

For applying an inclination to both or any one of the optical system on the measurement side and the optical system on the reference side, for example, the mirror 32 or the mirror 42 may be inclined, or any one of the lenses may be inclined, or a wedge-shaped prism having different thicknesses along a predetermined direction may be inserted on the optical path.

$A_1$ and $A_2$ are obtained from the light receiving intensities $V_1$ to $V_4$ by the following Formula (8), and a ratio of $A_1$ and $A_2$ is obtained by the following Formula (9). Further, the interference intensity AC is expressed by the following Formula (10). From these Formulas, the phase difference $\Delta\phi$ in accordance with the optical path difference can be obtained, and the interference intensity AC can also be obtained. The control unit 72 may realize the above processes by a simple electric circuit.

[Formula 8]

$$A_1 = V_1 - V_3 = 2 \cdot AC \cdot \sin(\Delta\phi) \quad (8a)$$

$$A_2 = V_4 - V_2 = 2 \cdot AC \cdot \cos(\Delta\phi) \quad (8b)$$

[Formula 9]

$$\frac{A_1}{A_2} = \frac{2 \cdot AC \cdot \sin(\Delta\phi)}{2 \cdot AC \cdot \cos(\Delta\phi)} = \tan(\Delta\phi) \quad (9)$$

[Formula 10]

$$AC^2 = \left(\frac{A_1}{2}\right)^2 + \left(\frac{A_2}{2}\right)^2 \quad (10)$$

In this way, the control unit 72 obtains the phase difference in accordance with the optical path difference and also obtains the interference intensity, controls the optical path difference adjusting operation by the optical path difference adjusting unit (the piezo element 43, the stage 44), so that the optical path difference is made small on the basis of the obtained interference intensity, and the optical path difference is kept constant on the basis of the obtained phase difference. Further, when the optical path difference is adjusted, any one of the piezo element 43 and the stage 44 may be controlled, however, the optical path difference can be roughly adjusted by the control of the stage 44, and the optical path difference can be finely adjusted by the control of the piezo element 43.

When the optical path difference is made small on the basis of the obtained interference intensity, the stage 44 may be automatically moved. Further, the interference intensity may be notified to the user to move the stage 44 by the user's operation. For example, the interference intensity is displayed on the display unit of the image acquisition unit 71 or the control unit 72, or a display unit separately provided from these units so as to notify the interference intensity to the user. The display unit may be a visual unit such as a display, an LED bar, an analog panel meter, or a digital panel meter, or an auditory unit such as a buzzer or a speaker which outputs a sound having a magnitude in accordance with the interference intensity, or further a tactile unit such as a vibrator which gives vibrations having a magnitude in accordance with the interference intensity to the user. The user moves the stage 44 in order to increase the interference intensity which is displayed on the display unit.

When the interference intensity is increased, it is most important that the optical path difference is minimized. However, even in a case where the focus or the optical axis of the imaging system of any one of the optical system on the sample side (the optical system of the first split light) and the optical system on the reference side (the optical system of the second split light) are deviated, the interference intensity is reduced. Therefore, the first thing to do for increasing the interference intensity is to adjust the optical path difference to be reduced, and further, to adjust the focus and the optical axis of each imaging system of the optical system on the sample side and the optical system on the reference side.

As an algorithm for maximizing the interference intensity, it is considered a method in which one of adjustment mechanisms (the optical path difference, the focus, and the optical axis) is moved in one direction while recording the interference intensity, the adjustment mechanism is moved in the reverse direction when the interference intensity passes by an optimal position and begins to be lowered, and a point at which the interference intensity is obtained within several % of error in maximum intensity obtained during scanning in one direction is considered as an optimal value. In a case where there are a plurality of adjustment points, an algorithm is considered in which the searching of such an optimal value is performed sequentially on each of the adjustment points, the adjustment is performed once more or in plural times as needed after one cycle of adjustment so as to realize an optimal state of the optical system as a whole.

Third Embodiment

Figure 4:
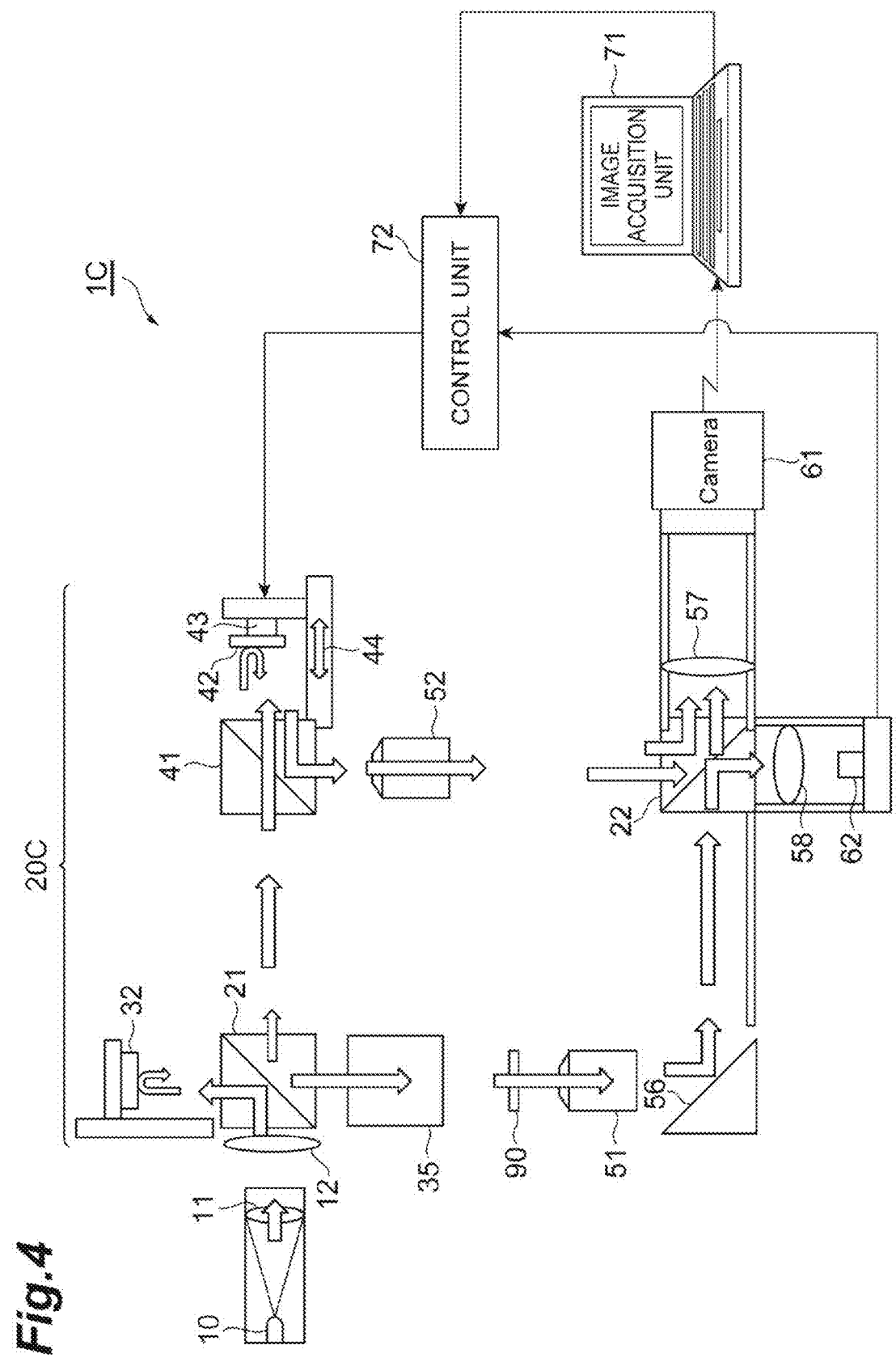
FIG. 4 is a diagram illustrating a configuration of an interference observation apparatus 1C of a third embodiment.

FIG. 4 is a diagram illustrating a configuration of an interference observation apparatus 1C of a third embodiment. The interference observation apparatus 1C of the third embodiment illustrated in FIG. 4 is a modification of the configuration illustrated in FIG. 3, and is different in the configuration of an interference optical system 20C from the splitting beam splitter 21 to the combining beam splitter 22. That is, the interference observation apparatus 1C of the third embodiment illustrated in FIG. 4 is different from the configuration illustrated in FIG. 3 in that the splitting beam splitter 21 also serves to perform the function of the beam splitter 31 in FIG. 3, the combining beam splitter 22 also serves to perform the function of the beam splitter 55 in FIG. 3, an optical path difference compensating plate 35 and a mirror 56 are provided, and a lens 57 and a lens 58 are provided in place of the tube lens 53. In the configuration illustrated in FIG. 4, the number of beam splitters is fewer by two compared to the configuration illustrated in FIG. 3, and thus it is possible to make cost down.

Fourth Embodiment

Figure 5:
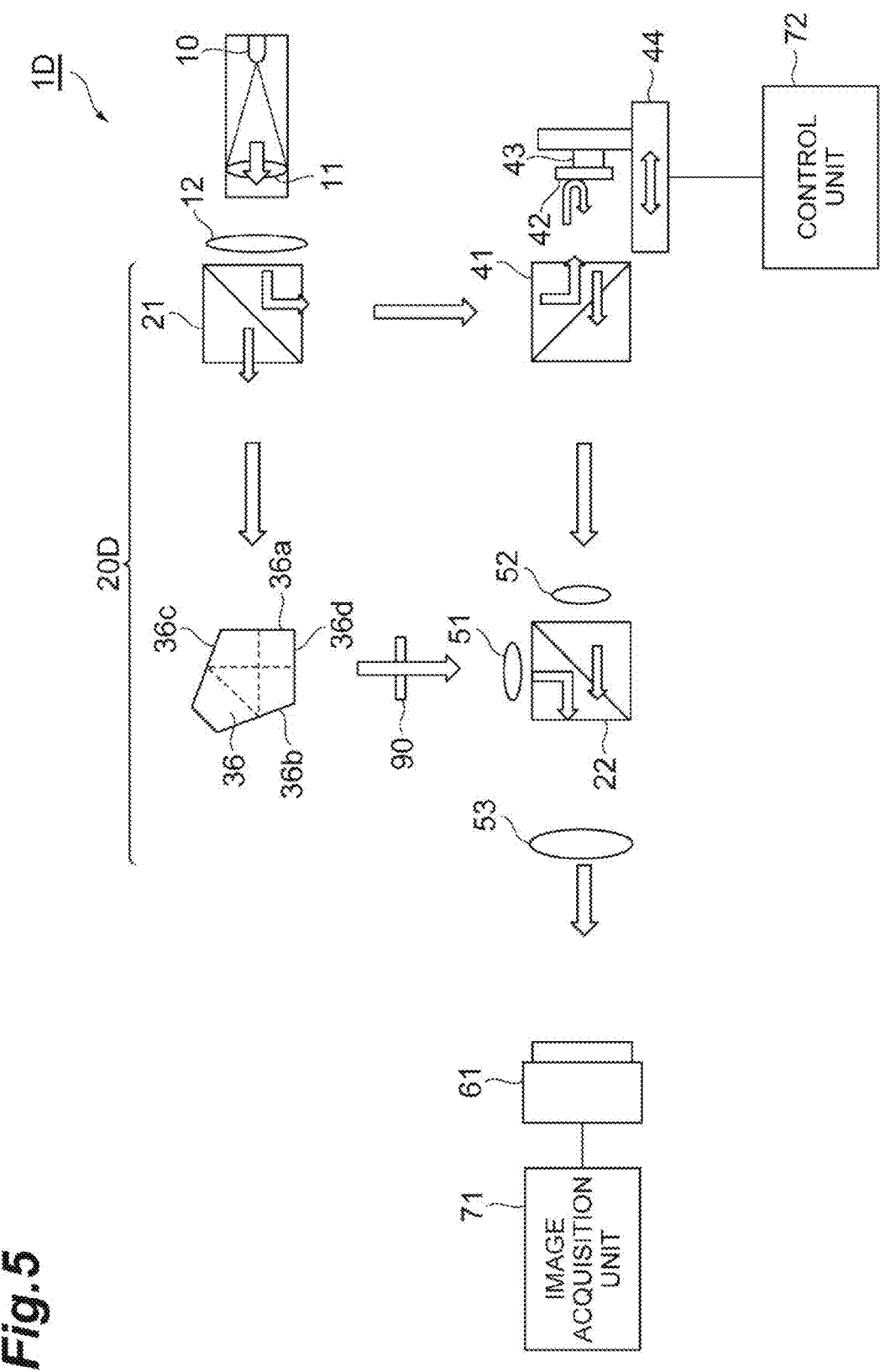
FIG. 5 is a diagram illustrating a configuration of an interference observation apparatus 1D of a fourth embodiment.

FIG. 5 is a diagram illustrating a configuration of an interference observation apparatus 1D of a fourth embodiment. The interference observation apparatus 1D includes a light source 10, a lens 11, a lens 12, a splitting beam splitter 21, a combining beam splitter 22, an image inverting prism 36, a beam splitter 41, a mirror 42, a piezo element 43, a stage 44, a lens 51, a lens 52, a tube lens 53, an imaging unit (light receiving unit) 61, an image acquisition unit 71, and a control unit 72. An interference optical system 20D from the splitting beam splitter 21 to the combining beam splitter 22 forms the Mach-Zehnder interferometer.

While the interference optical system 20A of the interference observation apparatus 1A of the first embodiment illustrated in FIG. 1 includes the beam splitter 31 and the mirror 32, the interference optical system 20D of the interference observation apparatus 1D of the fourth embodiment illustrated in FIG. 5 includes the image inverting prism 36. The image inverting prism 36 is provided in the optical system on the measurement side. The image inverting prism 36 is, for example, a penta prism.

The image inverting prism 36 is a polygonal pillar prism which includes a first side surface 36a, a second side surface 36b, a third side surface 36c, and a fourth side surface 36d. The image inverting prism 36 transmits the first split light arrived from the splitting beam splitter 21 into the inside from the first side surface 36a, and reflects the first split light sequentially by the second side surface 36b and the third side surface 36c, and then, the first split light is transmitted from the fourth side surface 36d to the outside, and output to the combining beam splitter 22.

In the present embodiment, the first split light is reflected twice in the image inverting prism 36, and the image is inverted twice. The second split light is reflected by the beam splitter 41 and the mirror 42, and the image is similarly inverted twice. The image inverting prism 36 is an optical element provided such that the total number of times of respective reflections of the first split light and the second split light is an even number. Similarly to the case of the first embodiment, the total number of times of image inversions by the respective reflections of the first split light and the second split light is an even number, and therefore, the directions of the respective images of the first split light and the second split light at the time of the combining by the combining beam splitter 22 are matched to each other, and the first split light and the second split light can interfere with high efficiency in a wide range of the imaging plane of the imaging unit 61.

Fifth Embodiment

Figure 6:
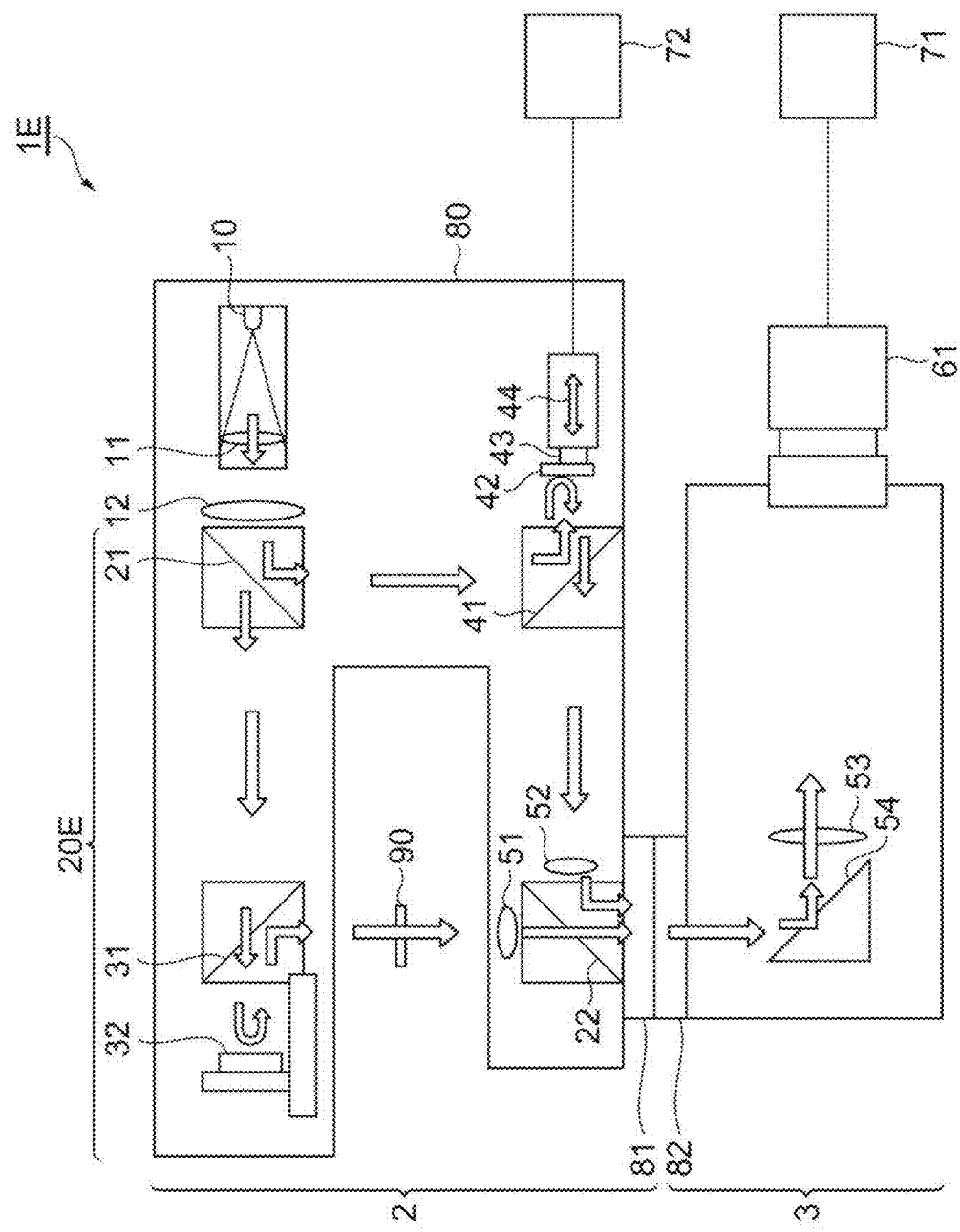
FIG. 6 is a diagram illustrating a configuration of an interference observation apparatus 1E of a fifth embodiment.

FIG. 6 is a diagram illustrating a configuration of an interference observation apparatus 1E of a fifth embodiment. The interference observation apparatus 1E includes a light source 10, a lens 11, a lens 12, a splitting beam splitter 21, a combining beam splitter 22, a beam splitter 31, a mirror 32, a beam splitter 41, a mirror 42, a piezo element 43, a stage 44, a lens 51, a lens 52, a tube lens 53, an imaging unit (light receiving unit) 61, an image acquisition unit 71, and a control unit 72. An interference optical system 20E from the splitting beam splitter 21 to the combining beam splitter 22 in the present embodiment forms the Mach-Zehnder interferometer, and has the configuration similar to that of the interference optical system 20A in the first embodiment.

In the present embodiment, the light source 10 and the interference optical system 20E are held by a housing 80. Further, a first attachment portion 81 is provided in the housing 80. The first attachment portion 81 includes an opening for outputting the combining light output from the combining beam splitter 22 of the interference optical system 20E to the outside. The light source 10, the interference optical system 20E, the housing 80, and the first attachment portion 81 constitute an interference optical apparatus 2.

Further, in the present embodiment, the tube lens 53, the imaging unit 61, the mirror 54, and a second attachment portion 82 constitute a microscope apparatus 3. The second attachment portion 82 includes an opening to be optically coupled to the opening of the first attachment portion 81, and freely performs the optical coupling with the first attachment portion 81. The imaging unit 61 receives the combined light output from the interference optical system 20E and outputs the detection signal. The combined light output from the interference optical system 20E is received by the imaging unit 61 through the opening of the first attachment portion 81, the opening of the second attachment portion 82, the mirror 54, and the tube lens 53. A commercially available apparatus may be used as the microscope apparatus 3. That is, the attachment portion for the objective lens in the normal commercially available microscope apparatus may be used as the second attachment portion 82 described above.

The interference observation apparatus 1E of the present embodiment may be configured by assembling the normal microscope apparatus 3 and the interference optical apparatus 2 in which the light source 10 and the interference optical system 20E are held by the housing 80 to be reduced in size and integrated. In the present embodiment, since the existing microscope apparatus 3 can be used, the interference observation apparatus 1E can be configured at a low cost.

In the present embodiment, the beam splitter 31, the observation object 90, the combining beam splitter 22, the opening of the first attachment portion 81, and the opening of the second attachment portion 82 are aligned vertically in a single line. Therefore, when the observation object 90 is irradiated by an illumination device provided above the beam splitter 31, a bright field image of the observation object 90 can be acquired by the imaging unit 61. Further, in a case where the microscope apparatus 3 is a fluorescence microscope, the observation object 90 is irradiated and excited by an excitation illumination device provided below the combining beam splitter 22, so that a fluorescence image of the observation object 90 can be acquired by the imaging unit 61.

Further, similarly to the configuration of the present embodiment, even in the interference observation apparatuses 1A to 1D of the first to fourth embodiments, the interference optical systems 20A to 20D from the splitting beam splitter 21 to the combining beam splitter 22 and the light source 10 may be held by the housing to form the interference optical apparatus, and the interference optical apparatus and the microscope apparatus 3 may be optically coupled to each other.

(Modifications)

The interference observation apparatus according to One aspect of the present invention is not limited to the above embodiments, and various modifications can be made.

The interference observation apparatus according to the above embodiment includes (1) a light source for outputting incoherent light, and (2) an interference optical system forming a Mach-Zehnder interferometer and including a splitting beam splitter for splitting the light output from the light source and outputting first split light and second split light, and a combining beam splitter for combining the first split light and the second split light and outputting combined light. In the interference observation apparatus, the interference optical system includes a second beam splitter and a second mirror on an optical path of the second split light, causes the second beam splitter to transmit or reflect the second split light arrived at the second beam splitter from the splitting beam splitter and then causes the second mirror to reflect the second split light, causes the second beam splitter to reflect or transmit the second split light reflected by the second mirror and arrived at the second beam splitter, and outputs the second split light from the second beam splitter in a direction different from an input direction of the second split light from the splitting beam splitter to the second beam splitter. The second mirror freely moves in a direction perpendicular to a reflecting surface of the second mirror. Further, the interference optical system includes an optical element on an optical path of the first split light such that the total number of times of respective reflections of the first split light and the second split light is an even number.

In the above interference observation apparatus, it is preferable that the interference optical system includes a first beam splitter and a first mirror as the optical element on the optical path of the first split light, causes the first beam splitter to transmit or reflect the first split light arrived at the first beam splitter from the splitting beam splitter and then causes the first mirror to reflect the first split light, causes the first beam splitter to reflect or transmit the first split light reflected by the first mirror and arrived at the first beam splitter, and outputs the first split light from the first beam splitter in a direction different from an input direction of the first split light from the splitting beam splitter to the first beam splitter.

The above interference observation apparatus preferably further includes a light receiving unit for receiving the combined light and outputting a detection signal.

The above interference observation apparatus preferably further includes an image acquisition unit for acquiring an interference image of an observation object on the optical path of the first split light or the second split light on the basis of the detection signal.

The above interference observation apparatus is preferably configured such that the observation object is disposed on any one of the optical paths of the first split light and the second split light, an optical path length/dispersion compensating plate is provided on the other optical path, and the optical path length/dispersion compensating plate compensates an influence of a change of an optical path length and a dispersion when the observation object is disposed.

The above interference observation apparatus is preferably configured such that the light source is an incoherent wavelength-variable light source, the light receiving unit receives the combined light for the light of each wavelength output from the light source and outputs the detection signal, and a wavelength dispersion of the observation object is obtained on the basis of the detection signal for each wavelength. Further, the above interference observation apparatus is also preferably configured such that the light source is an incoherent white light source, the light receiving unit receives the combined light for the light of each wavelength within an output band of the light source and outputs the detection signal, and a wavelength dispersion of the observation object is obtained on the basis of the detection signal for each wavelength.

The above interference observation apparatus preferably includes (1) a housing for holding the light source and the interference optical system, (2) a first attachment portion provided in the housing and having an opening for outputting the combined light output from the interference optical system to the outside, and (3) a microscope apparatus including a second attachment portion having an opening optically coupled to the opening of the first attachment portion, and a light receiving unit for receiving the combined light output from the interference optical system through the opening of the first attachment portion and the opening of the second attachment portion and outputting a detection signal.

Even any one of the first phase lock technique and the second phase lock technique may use a camera including a plurality of pixels arranged two-dimensionally as the photodetector 62 for the phase lock, so that the phase lock may be performed on the basis of the detection signal output from any one of the pixels.

Further, the phase lock may be performed on the basis of the detection signal output from any one of the pixels of the imaging unit 61. Further, there may be used one light receiving element which includes both of functions of the imaging unit 61 for acquiring the interference image and the photodetector 62 for the phase lock. In these cases, since the light receiving unit can be configured by one light receiving element, the apparatus can be made small, and the optical system can be easily adjusted.

Further, the interference intensity of the combined light may be obtained on the basis of the detection signal output from the imaging unit 61 for acquiring the interference image. Further, the interference intensity of the combined light may be obtained on the basis of the detection signals respectively output from the imaging unit 61 and the photodetector 62.

In a state where a plurality of interference fringes appear in an image captured by the imaging unit 61, any of pixels arranged two-dimensionally in the imaging unit 61 is considered as an alternative of the line sensor or the plurality of photodetectors arranged one-dimensionally, and the interference intensity may be obtained by the second phase lock technique. Alternatively, similarly to the first phase lock technique, the piezo element is modulated at a frequency sufficiently slow compared to an imaging speed of the imaging unit 61, and thus the interference intensity may be calculated by the above-described algorithm from a temporal variation of the interference image obtained by the imaging unit 61.

Further, the phase lock may also be performed by rapidly reading the detection signal from any of pixels of the imaging unit 61 without being limited to monitoring of the interference intensity. In recent years, a frame rate exceeding 1 kHz has been realized through technical renovations of a CCD camera and a CMOS camera, and such a frame rate is sufficient for deriving phase information even in any one case of the first phase lock technique and the second phase lock technique.

Further, a liquid crystal element (for example, a liquid crystal lens) or a prism, of which the refractive index or the geometrical thickness is changed according to an applying voltage value, may be inserted to any one or both of the optical path of the first split light and the optical path of the second split light from the splitting to the combining in the interference optical system, and even in this case, it is possible to adjust the optical path difference between the optical path of the first split light and the optical path of the second split light from the splitting to the combining in the interference optical system.

EXAMPLES

The description will be given about an example using the interference observation apparatus 1C having the configuration illustrated in FIG. 4. In this example, an LED having a wavelength of 580 nm is used as the light source 10. The lens 12 is configured to condense the light approximately on the front focal planes of the lenses 51 and 52. Since light transmits through a glass by additional one beam splitter in the optical system on the reference side, a glass plate having the same size as that of the beam splitter is inserted as the optical path difference compensating plate 35 in the optical system on the object side. The objective lenses of the magnification of 20 are used as the lenses 51 and 52.

A camera equipped with the CCD area image sensor is used as the imaging unit 61. Further, a photodiode is used as the photodetector 62. All the optical elements from the splitting beam splitter 21 to the lenses 51 and 52 are configured to have apertures to sufficiently cover the beam diameter of the LED light at the positions.

A dried and fixed confluent HeLa cell is used as the observation object. At the time of observation, several drops of pure water are trickled onto the cell, a cover glass is set thereon, and the cell is observed by the objective lens 51 from the lower side.

The angular frequency co of the vibration of the mirror 42 caused by the piezo element 43 is set to 2.3 kHz. The components of 2.3 kHz and 4.6 kHz in the detection signal output from the photodetector 62 are synchronously detected by the control unit 72. The phase difference $\Delta\phi$ is obtained from the above Formula (5) on the basis of the synchronous detection result, and the center position of the vibration of the mirror 42 caused by the piezo element 43 is subjected to the feedback control on the basis of the phase difference $\Delta\phi$ to perform the phase lock and the phase shift.

Figure 7:
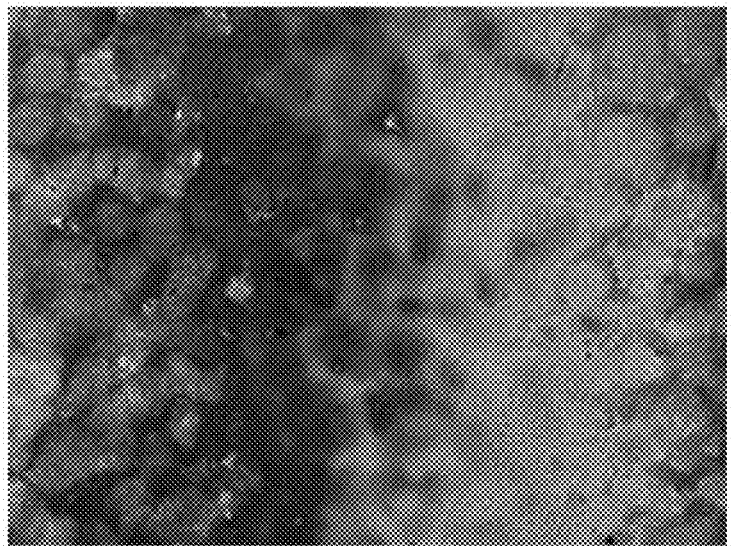
FIG. 7 includes views showing interference images.
Figure 7:
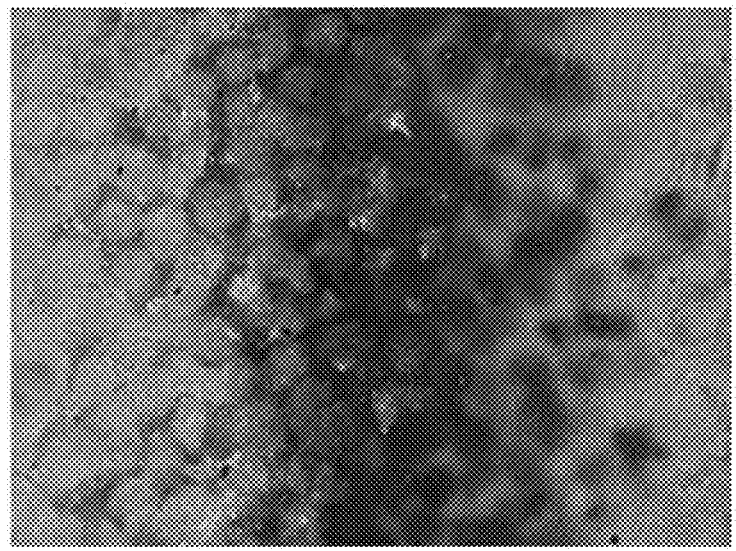
Figure 8:
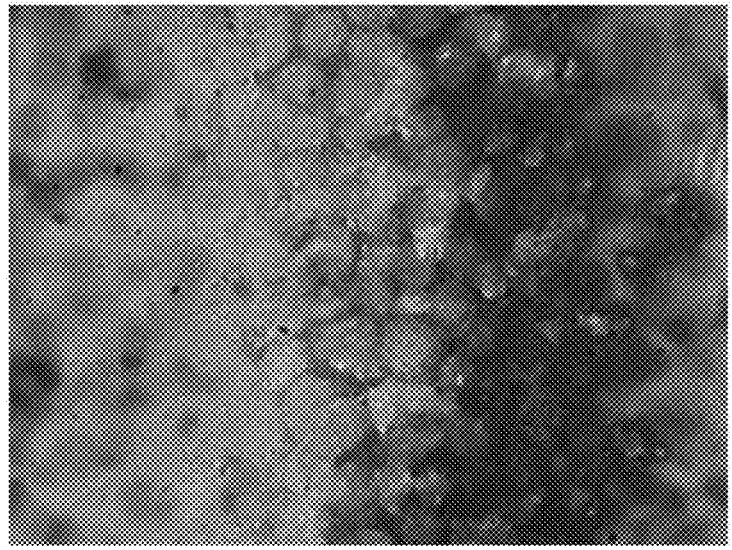
FIG. 8 includes views showing interference images.
Figure 8:
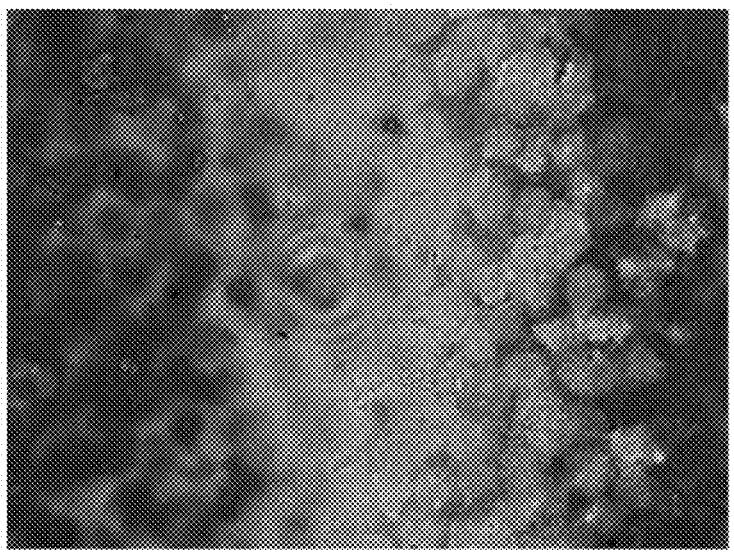
Figure 9:
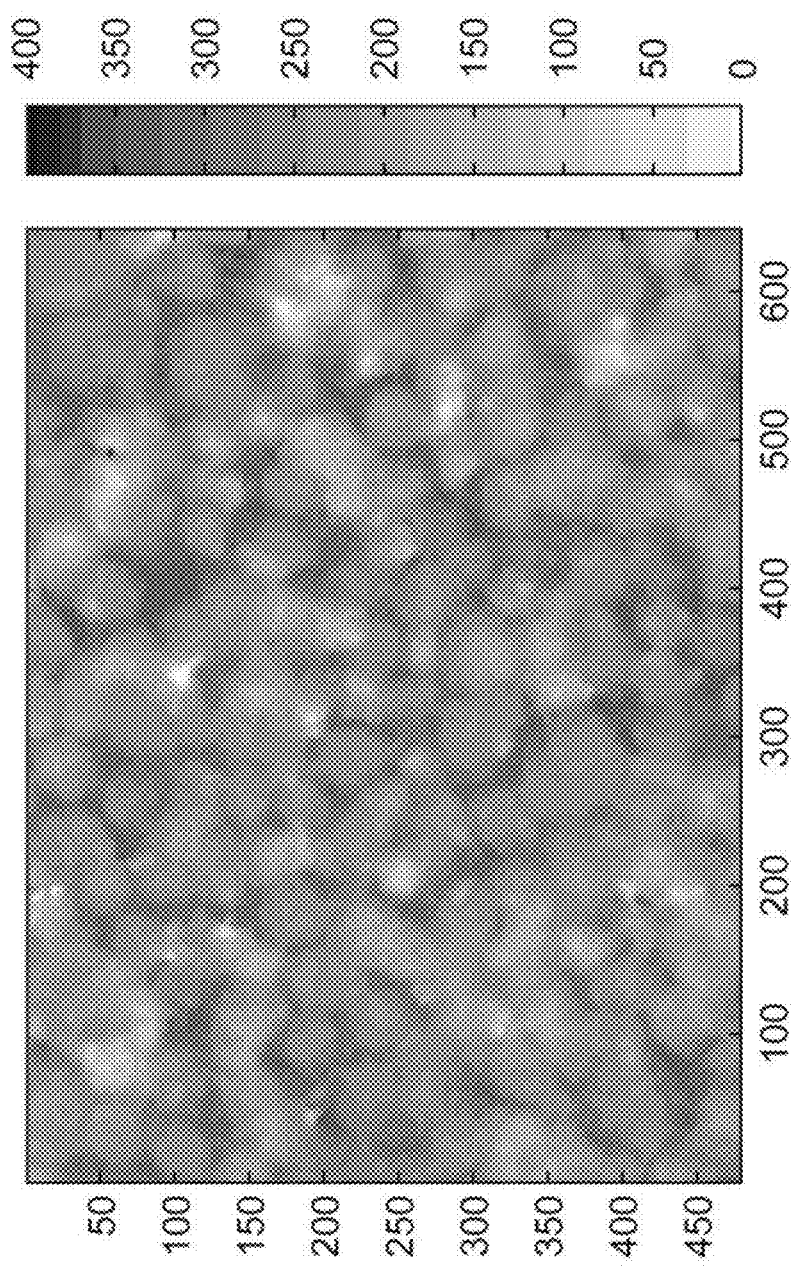
FIG. 9 is a view showing a phase image.

FIG. 7 and FIG. 8 include views showing the interference images acquired by performing the phase shift and the phase lock. An interference image $I_2(x, y)$ shown in (b) in FIG. 7 is different from an interference image $I_1(x, y)$ shown in (a) in FIG. 7 in phase by $\pi/2$, an interference image $I_3(x, y)$ shown in (a) in FIG. 8 is different in phase by $\pi$, and an interference image $I_4(x, y)$ shown in (b) in FIG. 8 is different in phase by $3\pi/2$. A quantitative phase image $\psi(x, y)$ is obtained from these interference images $I_1$ to $I_4$ by the following Formula (11). Further, x and y are variables indicating the positions in the respective images. The image $\psi(x, y)$ is subjected to phase unwrapping, and a distortion component of the background is flattened by the calculation of the shading correction using a Zernike polynomial, so that the quantitative phase image shown in FIG. 9 is obtained.

[Formula 11]

$$\psi(x, y) = \tan^{-1}\left(\frac{I_1(x, y) - I_3(x, y)}{I_4(x, y) - I_2(x, y)}\right) \quad (11)$$

INDUSTRIAL APPLICABILITY

One aspect of the present invention is possible to be used as an interference observation apparatus which has a function of adjusting an optical path difference using an optical system of a Mach-Zehnder interferometer, is able to acquire an image having a high spatial resolution, and is easily made small in size.

REFERENCE SIGNS LIST 1A-1E—interference observation apparatus, 2—interference optical apparatus, 3—microscope apparatus, 10—light source, 11, 12—lens, 20A-20E—interference optical system, 21—splitting beam splitter, 22—combining beam splitter, 31—first beam splitter, 32—first mirror, 35—optical path difference compensating plate, 36—image inverting prism, 41—second beam splitter, 42—second mirror, 43—piezo element, 44—stage, 45—stage, 51, 52—lens, 53—tube lens, 54—mirror, 55—beam splitter, 56—mirror, 57, 58—lens, 61—imaging unit (light receiving unit), 62—photodetector (light receiving unit), 71—image acquisition unit, 72—control unit, 80—housing, 81—first attachment portion, 82—second attachment portion, 90—observation object (sample), 91—optical path length/dispersion compensating plate.

The invention claimed is:

1. An interference observation apparatus, comprising:
a light source configured to output incoherent light; and
an interference optical system forming a Mach-Zehnder interferometer and including a splitting beam splitter configured to split the light output from the light source to output first split light and second split light, and a combining beam splitter configured to combine the first split light and the second split light to output combined light, wherein
the interference optical system
includes a second beam splitter and a second mirror on an optical path of the second split light, is configured to cause the second beam splitter to transmit or reflect the second split light arrived at the second beam splitter from the splitting beam splitter and then cause the second mirror to reflect the second split light, cause the second beam splitter to reflect or transmit the second split light reflected by the second mirror and arrived at the second beam splitter, output the second split light from the second beam splitter in a direction different from an input direction of the second split light from the splitting beam splitter to the second beam splitter, and freely move the second mirror in a direction perpendicular to a reflecting surface of the second mirror,
includes an optical element on an optical path of the first split light such that the total number of times of respective reflections of the first split light and the second split light is an even number, and
includes a first beam splitter and a first mirror as the optical element on the optical path of the first split light, is configured to cause the first beam splitter to transmit or reflect the first split light arrived at the first beam splitter from the splitting beam splitter and then cause the first mirror to reflect the first split light, cause the first beam splitter to reflect or transmit the first split light reflected by the first mirror and arrived at the first beam splitter, and output the first split light from the first beam splitter in a direction different from an input direction of the first split light from the splitting beam splitter to the first beam splitter.

2. The interference observation apparatus according to claim 1, further comprising a light receiving unit configured to receive the combined light and output a detection signal.

3. The interference observation apparatus according to claim 2, further comprising an image acquisition unit configured to acquire an interference image of an observation object on the optical path of the first split light or the second split light on the basis of the detection signal.

4. The interference observation apparatus according to claim 3, wherein the observation object is disposed on any one of the optical paths of the first split light and the second split light, and an optical path length/dispersion compensating plate is provided on the other optical path, and
the optical path length/dispersion compensating plate is configured to compensate an influence of a change of an optical path length and a dispersion when the observation object is disposed.

5. The interference observation apparatus according to claim 3, wherein the light source is an incoherent wavelength variable light source,
   the light receiving unit is configured to receive the combined light for the light of each wavelength output from the light source and output the detection signal, and
   a wavelength dispersion of the observation object is obtained on the basis of the detection signal for each wavelength.

6. The interference observation apparatus according to claim 3, wherein the light source is an incoherent white light source,
   the light receiving unit is configured to receive the combined light for the light of each wavelength within an output band of the light source and output the detection signal, and
   a wavelength dispersion of the observation object is obtained on the basis of the detection signal for each wavelength.

7. The interference observation apparatus according to claim 1, comprising
   a housing configured to hold the light source and the interference optical system;
   a first attachment portion provided in the housing and having an opening configured to output the combined light output from the interference optical system to the outside; and
   a microscope apparatus including a second attachment portion having an opening optically coupled to the opening of the first attachment portion, and a light receiving unit configured to receive the combined light output from the interference optical system through the opening of the first attachment portion and the opening of the second attachment portion, and output a detection signal.

* * * * *